(12) United States Patent
Greenfield

(10) Patent No.: US 12,139,729 B2
(45) Date of Patent: *Nov. 12, 2024

(54) NEURODEGENERATIVE DISORDERS

(71) Applicant: NEURO-BIO LTD, Oxford (GB)

(72) Inventor: Susan Greenfield, Oxford (GB)

(73) Assignee: NEURO-BIO LTD, Oxford (GB)

( * ) Notice: Subject to any disclaimer, the term of this patent is extended or adjusted under 35 U.S.C. 154(b) by 356 days.

This patent is subject to a terminal disclaimer.

(21) Appl. No.: 17/374,227

(22) Filed: Jul. 13, 2021

(65) Prior Publication Data

US 2021/0388331 A1   Dec. 16, 2021

Related U.S. Application Data

(63) Continuation of application No. 15/999,129, filed on Aug. 17, 2018, now Pat. No. 11,091,747, which is a continuation of application No. 14/903,589, filed as application No. PCT/GB2014/052041 on Jul. 4, 2014, now Pat. No. 10,053,677.

(30) Foreign Application Priority Data

Jul. 9, 2013   (GB) ...................................... 1312279

(51) Int. Cl.
| | |
|---|---|
| *C12N 9/18* | (2006.01) |
| *A61K 38/00* | (2006.01) |
| *A61K 38/12* | (2006.01) |
| *C07K 7/08* | (2006.01) |
| *C07K 7/64* | (2006.01) |
| *C12N 9/16* | (2006.01) |
| *G01N 33/50* | (2006.01) |

(52) U.S. Cl.
  CPC ................ *C12N 9/18* (2013.01); *A61K 38/12* (2013.01); *C07K 7/08* (2013.01); *C07K 7/64* (2013.01); *C12N 9/16* (2013.01); *C12Y 301/01007* (2013.01); *G01N 33/5058* (2013.01); *A61K 38/00* (2013.01)

(58) Field of Classification Search
  None
  See application file for complete search history.

(56) References Cited

U.S. PATENT DOCUMENTS

| | | | |
|---|---|---|---|
| 5,777,073 A | 7/1998 | Rivier | |
| 10,053,677 B2 * | 8/2018 | Greenfield | ......... G01N 33/5058 |
| 11,091,747 B2 * | 8/2021 | Greenfield | .............. A61P 25/16 |

FOREIGN PATENT DOCUMENTS

| | | |
|---|---|---|
| WO | WO-00/73427 A2 | 12/2000 |
| WO | WO-01/49107 A1 | 7/2001 |
| WO | WO-02/14351 A2 | 2/2002 |

OTHER PUBLICATIONS

Sanghai N, Tranmer GK. Biochemical and Molecular Pathways in Neurodegenerative Diseases: An Integrated View. Cells. 2023; 12(18):2318. https://doi.org/10.3390/cells12182318 (Year: 2023).*

(Continued)

*Primary Examiner* — Daniel E Kolker
*Assistant Examiner* — Hilary Ann Petrash
(74) *Attorney, Agent, or Firm* — SQUIRE PATTON BOGGS (US) LLP

(57) ABSTRACT

A cyclic polypeptide, derivative or analogue thereof, comprising an amino acid sequence derived from the C-terminus of acetylcholinesterase (AChE), or a truncation thereof.

1 Claim, 18 Drawing Sheets
Specification includes a Sequence Listing.

(56) References Cited

OTHER PUBLICATIONS

Huntington's Disease. Huntington's Disease: What It Is, Symptoms & Treatment (clevelandclinic.org) (accessed Oct. 28, 2023) (Year: 2023).*
Parkinson's Disease. Parkinson's Disease: What It Is, Causes, Symptoms & Treatment (clevelandclinic.org) (accessed Oct. 28, 2023) (Year: 2023).*
Durães F, Pinto M, Sousa E. Old Drugs as New Treatments for Neurodegenerative Diseases. Pharmaceuticals. 2018; 11(2):44. https://doi.org/10.3390/ph11020044 (Year: 2018).*
Amna Akhtar et al. Neurodegenerative diseases and effective drug delivery: A review of challenges and novel therapeutics, Journal of Controlled Release, vol. 330, 2021, pp. 1152-1167, ISSN 0168-3659, https://doi.org/10.1016/j.jconrel.2020.11.021. (Year: 2021).*
Lamptey RNL, Chaulagain B, Trivedi R, Gothwal A, Layek B, Singh J. A Review of the Common Neurodegenerative Disorders: Current Therapeutic Approaches and the Potential Role of Nanotherapeutics. International Journal of Molecular Sciences. 2022; 23 (3):1851. https://doi.org/10.3390/ijms23031851 (Year: 2022).*
Teshome L. Aboye, Julio A. Camarero, Biological Synthesis of Circular polypeptides*, Journal of Biological Chemistry, vol. 287, Issue 32, 2012, pp. 27026-27032, ISSN 0021-9258, https://doi.org/10.1074/jbc.R111.305508. https://www.sciencedirect.com/science/article/pii/S0021925820478962 (Year: 2012).*
Garcia-Ratés et al. (2016). (I) Pharmacological profiling of a novel modulator of the α7 nicotinic receptor: Blockade of a toxic acetylcholinesterase-derived peptide increased in Alzheimer brains. Neuropharmacology, 105, 487-499 (Year: 2016).*
Zimmermann, M. (2013). Neuronal AChE splice variants and their non-hydrolytic functions: redefining a target of AChE inhibitors?. British journal of pharmacology, 170(5), 953-967 (Year: 2013).*
Clark et al. (2005). Engineering stable peptide toxins by means of backbone cyclization: stabilization of the α-conotoxin MII. Proceedings of the National Academy of Sciences, 102(39), 13767-13772 (Year: 2005).*
Roxin et al. Flexible or fixed:a comparative review of linear and cyclic cancer-targeting peptides. Future Med. Chem. 2012. 4(12), 1601-1618 (Year: 2012).*
International Search Report and Written Opinion in PCT/GB2014/052041 dated Sep. 19, 2014, 12 pages.
UKIPO Search Report for Application No. GB1312279.1 dated Apr. 15, 2014, 3 pages.
B. Wu et al, "Structures of the CXCR4 Chemokine GPCR with Small-Molecule and Cyclic Peptide Antagonists", *Science*, 2010, vol. 330, pp. 1066-1071.
M.I. Fonseca et al, "Treatment with a C5aR Antagonist Decreases Pathology and Enhances Behavioral Performance in Murine Models of Alzheimers Disease", *J Immunology*, 2009, vol. 183, pp. 1375-1383.
C.E. Bond et al., "Upregulation of Alpha 7 Nicotinic Receptors by Acetylcholinesterase C-Terminal Peptides", PLoS ONE, vol. 4, No. 3, Mar. 16, 2009, p. e4846, XP055138903.
Greenfield Susan, "Discovering and Targeting the Basic Mechanism of Neurodegeneration: The Role of Peptides From The C-Terminus Of Acetylcholinesterase Non-Hydrolytic Effects Of Ache: The Actions Of Peptides Derived From The C-Terminal and Their Relevance To Neurodegeneration", *Chemico-Biological Interactions*, Apr. 3, 2013, vol. 203, No. 3, pp. 543-546.

* cited by examiner

Figure 11
```
Aβ    DAEFR HDSGY EVHHQ KLVFF AEDVG SNKGA IIGLM VGGVV IA
T30   KAEFR RWSSY MVHWK NQFDH YSKQD RCSDL
T14   AEFR  RWSSY MVHWK
T15                     NQFDH YSKQD RCSDL
```
Figure 12
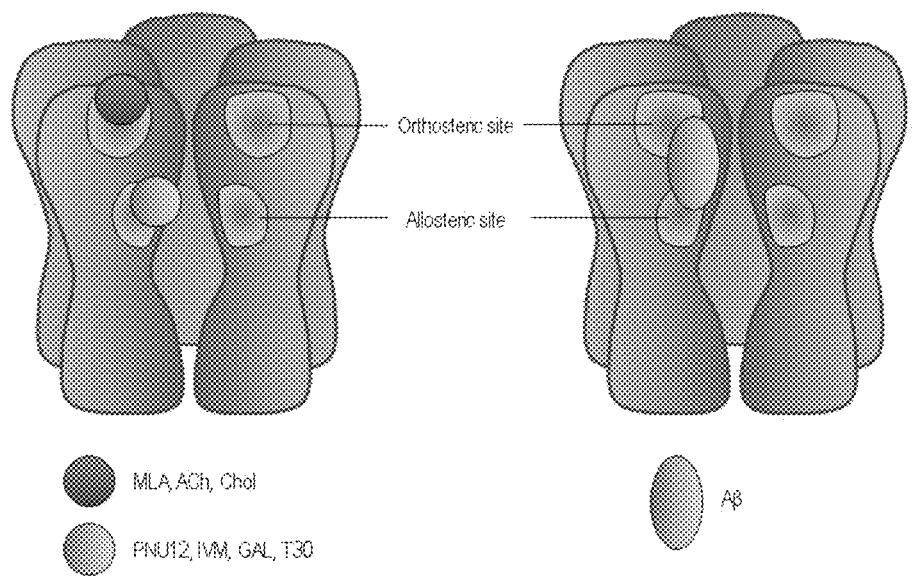
Figure 13
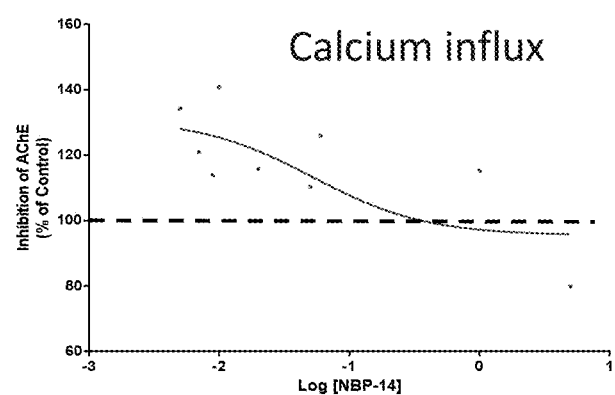

SEQUENCE LISTING

<160> NUMBER OF SEQ ID NOS: 6

<210> SEQ ID NO 1
<211> LENGTH: 614
<212> TYPE: PRT
<213> ORGANISM: Homo sapiens

<400> SEQUENCE: 1

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

```
Arg Gly Ile Arg Leu Lys Thr Pro Gly Pro Val Ser Ala Phe Leu
 50              55              60
Gly Ile Pro Phe Ala Glu Pro Pro Met Gly Pro Arg Arg Phe Leu Pro
 65                  70              75                  80
Pro Glu Pro Lys Gln Pro Trp Ser Gly Val Val Asp Ala Thr Thr Phe
                 85              90                  95
Gln Ser Val Cys Tyr Gln Tyr Val Asp Thr Leu Tyr Pro Gly Phe Glu
                 100             105             110
Gly Thr Glu Met Trp Asn Pro Asn Arg Glu Leu Ser Glu Asp Cys Leu
             115             120             125
Tyr Leu Asn Val Trp Thr Pro Tyr Pro Arg Pro Thr Ser Pro Thr Pro
 130             135             140
Val Leu Val Trp Ile Tyr Gly Gly Phe Tyr Ser Gly Ala Ser Ser
 145             150             155             160
Leu Asp Val Tyr Asp Gly Arg Phe Leu Val Gln Ala Glu Arg Thr Val
                 165             170             175
Leu Val Ser Met Asn Tyr Arg Val Gly Ala Phe Gly Phe Leu Ala Leu
             180             185             190
Pro Gly Ser Arg Glu Ala Pro Gly Asn Val Gly Leu Leu Asp Gln Arg
         195             200             205
Leu Ala Leu Gln Trp Val Gln Glu Asn Val Ala Ala Phe Gly Gly Asp
 210             215             220
Pro Thr Ser Val Thr Leu Phe Gly Glu Ser Ala Gly Ala Ala Ser Val
 225             230             235             240
Gly Met His Leu Leu Ser Pro Pro Ser Arg Gly Leu Phe His Arg Ala
             245             250             255
Val Leu Gln Ser Gly Ala Pro Asn Gly Pro Trp Ala Thr Val Gly Met
             260             265             270
Gly Glu Ala Arg Arg Arg Ala Thr Gln Leu Ala His Leu Val Gly Cys
         275             280             285
Pro Pro Gly Gly Thr Gly Gly Asn Asp Thr Glu Leu Val Ala Cys Leu
         290             295             300
Arg Thr Arg Pro Ala Gln Val Leu Val Asn His Glu Trp His Val Leu
 305             310             315             320
Pro Gln Glu Ser Val Phe Arg Phe Ser Phe Val Pro Val Val Asp Gly
                 325             330             335
Asp Phe Leu Ser Asp Thr Pro Glu Ala Leu Ile Asn Ala Gly Asp Phe
             340             345             350
His Gly Leu Gln Val Leu Val Gly Val Val Lys Asp Glu Gly Ser Tyr
             355             360             365
Phe Leu Val Tyr Gly Ala Pro Gly Phe Ser Lys Asp Asn Glu Ser Leu
 370             375             380
Ile Ser Arg Ala Glu Phe Leu Ala Gly Val Arg Val Gly Val Pro Gln
 385                 390             395             400
Val Ser Asp Leu Ala Ala Glu Ala Val Val Leu His Tyr Thr Asp Trp
                 405             410             415
Leu His Pro Glu Asp Pro Ala Arg Leu Arg Glu Ala Leu Ser Asp Val
             420             425             430
Val Gly Asp His Asn Val Val Cys Pro Val Ala Gln Leu Ala Gly Arg
             435             440             445
Leu Ala Ala Gln Gly Ala Arg Val Tyr Ala Tyr Val Phe Glu His Arg
 450             455             460
Ala Ser Thr Leu Ser Trp Pro Leu Trp Met Gly Val Pro His Gly Tyr
```

```
                465                 470                 475                 480
Glu Ile Glu Phe Ile Phe Gly Ile Pro Leu Asp Pro Ser Arg Asn Tyr
                    485                 490                 495

Thr Ala Glu Glu Lys Ile Phe Ala Gln Arg Leu Met Arg Tyr Trp Ala
                500                 505                 510

Asn Phe Ala Arg Thr Gly Asp Pro Asn Glu Pro Arg Asp Pro Lys Ala
            515                 520                 525

Pro Gln Trp Pro Pro Tyr Thr Ala Gly Ala Gln Tyr Val Ser Leu
        530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
                580                 585                 590

Ser Tyr Met Val His Trp Lys Asn Gln Phe Asp His Tyr Ser Lys Gln
                595                 600                 605

Asp Arg Cys Ser Asp Leu
        610

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 30
<212> TYPE: PRT
<213> ORGANISM: Homo sapiens

<400> SEQUENCE: 3

Lys Ala Glu Phe His Arg Trp Ser Ser Tyr Met Val His Trp Lys Asn
1               5                   10                  15

Gln Phe Asp His Tyr Ser Lys Gln Asp Arg Cys Ser Asp Leu
            20                  25                  30

<210> SEQ ID NO 4
<211> LENGTH: 14
<212> TYPE: PRT
<213> ORGANISM: Homo sapiens

<400> SEQUENCE: 4

Ala Glu Phe His Arg Trp Ser Ser Tyr Met Val His Trp Lys
1               5                   10

<210> SEQ ID NO 5
<211> LENGTH: 15
<212> TYPE: PRT
<213> ORGANISM: Homo sapiens

<400> SEQUENCE: 5
```

```
Asn Gln Phe Asp His Tyr Ser Lys Gln Asp Arg Cys Ser Asp Leu
1               5                   10                  15

<210> SEQ ID NO 6
<211> LENGTH: 12
<212> TYPE: PRT
<213> ORGANISM: Homo sapiens
<220> FEATURE:
<221> NAME/KEY: misc_feature
<222> LOCATION: (4)..(4)
<223> OTHER INFORMATION: 'X' can be a basic amino acid residue,
      preferably histidine (H)
<220> FEATURE:
<221> NAME/KEY: misc_feature
<222> LOCATION: (5)..(5)
<223> OTHER INFORMATION: "X" can be a basic amino acid residue,
      preferably arginine (R)
<220> FEATURE:
<221> NAME/KEY: misc_feature
<222> LOCATION: (6)..(6)
<223> OTHER INFORMATION: "X" can be an aromatic amino acid residue,
      preferably tryptophan (W)
<220> FEATURE:
<221> NAME/KEY: misc_feature
<222> LOCATION: (8)..(8)
<223> OTHER INFORMATION: "X" can be an amino acid residue having an
      aliphatic hydroxyl side chain, preferably serine (S)
<220> FEATURE:
<221> NAME/KEY: misc_feature
<222> LOCATION: (10)..(10)
<223> OTHER INFORMATION: "X" can be tryptophan (W) or methionine (M)

<400> SEQUENCE: 6

Ala Glu Phe Xaa Xaa Xaa Ser Xaa Tyr Xaa Val His
1               5                   10
```

NEURODEGENERATIVE DISORDERS

This application is a continuation of U.S. patent application Ser. No. 15/999,129, filed Aug. 17, 2018, which is a continuation of U.S. patent application Ser. No. 14/903,589, filed Jan. 7, 2016, which in turn is a U.S. National Stage under 35 U.S.C. § 371 of International Application No. PCT/GB2014/052041, filed Jul. 4, 2014, which claims the benefit under 35 U.S.C. § 119(a) of Application No. GB 1312279.1, filed Jul. 9, 2013. The contents of these applications are hereby incorporated by reference in their entireties.

This application includes an electronically submitted sequence listing in .txt format. The .txt file contains a sequence listing entitled "019236_00036-Sequence-Listing," created Jul. 13, 2021, and is 7.27 kilobytes in size. The sequence listing contained in this .txt file is part of the specification and is incorporated herein by reference in its entirety.

The invention relates to neurodegenerative disorders, and in particular to novel compositions, therapies and methods for treating such conditions, for example Alzheimer's disease.

Alzheimer's disease primarily affects men and women over the age of 65 and the likelihood of being diagnosed with the disease increases substantially with age. With the percentage of adults over the age of 65 expected to grow worldwide over the next 40 years, the incidence of Alzheimer's disease is expected to more than double, escalating from 21 million cases in 2010 to 53 million in 2050 (statistics from www.alzheimersresearchuk.org and www.alz.org). This exponential increase in the expected number of patients presenting with Alzheimer's disease not only represents a major area of unmet medical need, but offers a significant market opportunity for therapeutics and diagnostics as there is currently no fully effective method of treating the disease.

There has been no new drug to combat Alzheimer's disease specifically, nor neurodegeneration more generally, in the last 10 years. The reason is that as yet, the basic underlying brain mechanism has not yet been identified that could consequently be targeted pharmaceutically. The main contender for accounting for the process of neurodegeneration is the 'amyloid hypothesis', where neuronal death is attributed to disruption of the cell membrane by toxic deposits of amyloid, characteristic of post-mortem Alzheimer brain, and resulting from abnormal cleavage of amyloid precursor protein. However, this 'amyloid hypothesis' does not explain the co-pathology frequently observed with Alzheimer's and Parkinson's diseases, nor the characteristic selectivity of cells vulnerable to degeneration, nor the absence of amyloid deposits in animal models of dementia, nor indeed the occurrence of amyloid in certain brain regions where cognitive deficits are not apparent. Despite the popularity of amyloid formation as a pharmaceutical target over the last two decades, no treatment based on this theory has as yet proved effective. A more likely possibility is that once the neurodegenerative process is underway, then amyloid will additionally be generated as a secondary, exacerbating effect that is less specific.

One clue for identifying the primary mechanism of neurodegeneration, could be that only various neuronal groups are primarily vulnerable. Moreover, the diverse cell sub-groups prone to Alzheimer's, Parkinson's and Motor Neurone Diseases nonetheless are adjacent to each other and form a continuous 'hub' extending from brainstem to forebrain that all send diffuse projections upwards and outwards to higher cerebral centres. Hence, despite their heterogeneity in transmitters, these neuronal groups have been collectively dubbed 'Global' neurons to distinguish them from the more familiar and localised circuits of cells in most other parts of the brain, such as cerebellum, thalamus, cortex etc. These selectively vulnerable Global neurons were previously identified, albeit using a different terminology ('isodendritic core') as pivotal in neurodegeneration several decades ago.

The sub-groups of Global neurons have a specific feature in common that might explain the puzzling and as yet unanswered question as to why only these cells succumb to progressive death whilst their counterparts elsewhere in the brain, even when damaged by stroke, do not: they retain a robust plasticity into and throughout adulthood, accompanied by a specific sensitivity to substances aiding and sustaining growth—'trophic factors'. In the developing brain, trophic factors work by stimulating calcium influx, which triggers a cascade of events within the cell, eventually resulting in selective differentiation and growth. However, in higher doses or with longer exposures, sustained calcium entry can be toxic to neurons. Most significantly, a further determining factor in whether or not calcium entry triggers trophic or toxic effects, is age: as neurons mature, an erstwhile trophic level of intracellular calcium becomes lethal.

The inventor has previously proposed that the neurodegenerative process is in fact an aberrantly activated process of development. In support of this hypothesis, a hypertrophy of the brainstem 'hub' neurons has actually been reported in Alzheimer brains (Bowser et al., 1997, Brain Pathol. 7:723-30). If large areas of this hub are damaged, then more than one neurodegenerative disease will present, as occurs in the frequently seen but never as yet explained cases of co-pathology with Alzheimer's and Parkinson's diseases. Interestingly, all the neurons within the vulnerable hub of Global neurons, despite transmitter heterogeneity, all contain the familiar enzyme acetylcholinesterase (AChE). AChE is therefore present in neurons where it would be unable to perform its normal function, since such sub-groups of cells as the noradrenergic locus coeruleus, the dopaminergic substantia nigra, or the serotonergic raphe nuclei, in no cases contain the usual substrate, acetylcholine. A further unexpected deviation from its normal, enzymatic role is that the AChE is actually released from Global neurons, presumably as some kind of inter-cellular messenger in its own right. In general, AChE is now widely and well-established as a signalling molecule that has trophic activity in a diverse variety of situations in both neural and non-neural tissue.

The inventor has previously shown that AChE, operating as a trophic agent independent of its enzymatic action, does indeed trigger calcium entry into neurons. It is possible therefore that within Global neurons, AChE has a dual non-classical action that ranges along a trophic-toxic axis, depending on amount, duration of availability and, most significantly, age. If standard neurons are damaged in adulthood, as in a stroke, others will compensate functionally. In contrast, Global neurons will respond by calling on their trophic resources in an attempt to regenerate. But because the subsequent calcium influx will be lethal in the older, mature cells, the resulting damage will trigger further attempts to compensate in a pernicious cycle that characterises neurodegeneration.

Acetylcholinesterase (AChE) is expressed at different stages of development in various forms, all of which have identical enzymatic activity, but which have very different molecular composition. The 'tailed' (T-AChE) is expressed at synapses and the inventors have previously identified two peptides that could be cleaved from the C-terminus, one referred to as "T14", within the other which is known as "T30", and which both have strong sequence homology to the comparable region of β-amyloid (see FIG. 11; and SEQ ID NO's: 2-5). The AChE C-terminal peptide "T14'" has been identified as being the salient part of the AChE molecule responsible for its range of non-hydrolytic actions. The synthetic 14 amino acids peptide analogue (i.e. "T14"), and subsequently the larger, more stable, and more potent amino acid sequence in which it is embedded (i.e. "T30") display actions comparable to those reported for 'non-cholinergic' AChE, where the inert residue within the T30 sequence (i.e. "T15") is without effect.

Acute effects of T14 and T30 are that they:—(i) modulate calcium entry into neurons in brain slices over time scales from milliseconds to hours; (ii) compromise cell viability in PC 12 cells and also in neuronal organotypic cultures in vitro. (iii) modulate 'compensatory' calcium-induced AChE release from neurons and PC 12 cells; (iv) activate calcium currents in oocytes and neurons in brain slices; (v) synergise with amyloid in toxic effects; and (vi) are involved in amyloid precursor protein production and amyloid beta peptide release. Chronic effects of T14 and T30 are that they:—(i) reduce neuron growth; (ii) induce apoptosis; (iii) increase AChE release; (iv) bind to and modulate α7 nicotinic-receptor; and (v) enhance expression of the α7 receptor on the cell surface over 24 hours, thereby providing a feedforward mechanism for further toxicity.

Since T14 and T30 are more selective than β-amyloid in inducing toxicity and are also synergistic with amyloid exacerbating toxicity, it has been postulated that any agent blocking the effect of T14 or T30 would also reduce the less selective and subsequent toxic effect of amyloid. The inventor has previously shown that T30 and T14 peptides bind to an allosteric site on the α7 nicotinic-receptor to induce a spectrum of trophic-toxic effects. This receptor is co-expressed with AChE during critical periods of brain development as well as showing a closely parallel distribution in the adult brain, and is one of the most powerful calcium ionophores in the brain. It can also function independent of cholinergic transmission, since choline (derived from diet) can serve as an alternative primary ligand. Moreover, this receptor has already been implicated in Alzheimer's disease as one of the targets for the current therapy galanthamine (Reminyl®), as well as being linked to the actions of amyloid.

However, the efficacy of galanthamine has proved limited, whilst other α7 nicotinic acetylcholine receptor antagonists are still in clinical trials. Galanthamine has a low affinity for the α7 nicotinic-receptor (i.e. only to μM) compared to that of T30 and T14, which have much higher affinities for the α7 nicotinic-receptor (i.e. 5 nM). Hence if, in an Alzheimer's brain, the endogenous equivalent of T30 peptide is already occupying the respective receptor site, galanthamine would need to be given at non-physiological, high doses with inevitable side effects and most importantly, questionable efficacy.

There is therefore a need to provide an improved medicament for the treatment of neurodegenerative disorders, such as Alzheimer's disease and Parkinson's disease.

As described in the Examples, the inventor has surprisingly demonstrated that cyclic forms of peptides derived from the C-terminus of AChE can be used to selectively inhibit the non-classical effects of AChE and/or its terminal peptide in vitro (i.e. the effects of AChE that are independent of its enzymatic activity), and therefore effectively treat neurodegenerative disorders.

Thus, according to a first aspect of the invention, there is provided a cyclic polypeptide, derivative or analogue thereof, comprising an amino acid sequence derived from the C-terminus of acetylcholinesterase (AChE), or a truncation thereof.

Cyclic polypeptides are peptide chains whose N- and C-termini are themselves linked together with a peptide bond that forms a circular chain of amino acids, and, to date, no cyclic peptides have been developed which comprise an amino acid sequence derived from the C-terminus of acetylcholinesterase (AChE), or a truncation thereof. As described in the Examples, the inventor has surprisingly demonstrated that the inefficacy of protection against the non-specific action of hydrogen peroxide would suggest that the blocking action of the cyclic polypeptide of the first aspect is highly selective, and receptor-mediated. The inventor was also very surprised to observe that the cyclic polypeptides of the invention antagonise the toxic effects of the known linear peptides, T14 and T30, in a variety of tests indicating that they prevent the additional influx of calcium through an allosteric site (e.g. an Ivermectin-sensitive allosteric site) of the α7 nicotinic-receptor and effectively outcompete binding for the linear T14 and T30 peptides, as well as β-amyloid. Therefore, the cyclic polypeptide, derivative or analogue thereof may be a selective antagonist of the α7 nicotinic-receptor.

However, the inventors have shown that the cyclic polypeptides of the invention act as an inert allosteric modulator of the α7 nicotinic-receptor which antagonises the action of T30 and amyloid beta peptides. Therefore, preferably the cyclic polypeptide, derivative or analogue thereof is a selective allosteric modulator of the α7 nicotinic-receptor, more preferably an inert selective allosteric modulator thereof. The term "inert" can mean that the polypeptide of the invention only acts as an allosteric modulator of the receptor in the presence of the toxic compounds, i.e. $T_{30}$ and amyloid beta peptides (β-amyloid).

Preferably, the cyclic polypeptide, derivative or analogue thereof prevents the additional influx of calcium through an allosteric site (most preferably, an Ivermectin-sensitive allosteric site) of the α7 nicotinic-receptor. It is preferred that the cyclic polypeptide, derivative or analogue thereof outcompetes binding for β-amyloid.

It could not have been predicted that the peptides of the invention would outcompete the endogenous equivalent of $T_{30}$ peptide already occupying the respective receptor site. Furthermore, the enhanced stability of cyclic peptides would account for this effective displacement. Accordingly, the cyclic polypeptide prevents the previously established toxic effects of the linear T14, T30 peptides and also β-amyloid. The inventor believes therefore that the cyclic polypeptides of the invention will have significant utility for the treatment of neurodegenerative disorders in stabilising any further cell loss.

The term "derivative or analogue thereof" can mean a polypeptide within which amino acid residues are replaced by residues (whether natural amino acids, non-natural amino acids or amino acid mimics) with similar side chains or peptide backbone properties.

The term "derived from" can mean an amino acid sequence which is a derivative or a modification of an amino acid sequence that is present in, or forms, the C-terminus of AChE, and portion thereof.

The term "truncation thereof" can mean the cyclic polypeptide derived from AChE is reduced in size by the removal of amino acids. The reduction of amino acids may be achieved by removal of residues from the C- or N-terminal of the peptide prior to cyclisation into the cyclic polypeptide of the invention, or may be achieved by deletion of one or more amino acids from within the core of the peptide prior to cyclisation.

Preferably, the cyclic polypeptide is purified and/or isolated, i.e. it is not found in nature.

Acetylcholinesterase is a serine protease that hydrolyses acetylcholine, and will be well-known to the skilled person. The major form of acetylcholinesterase which is found in the brain is known as tailed acetylcholinesterase (T-AChE). Given that the invention is primarily concerned with treating neurodegenerative disorders, it is preferred that the cyclic polypeptide, derivative or analogue thereof comprises an amino acid sequence derived from the C-terminus of tailed acetylcholinesterase (T-AChE), or a truncation thereof.

The protein sequence of one embodiment of human tailed acetylcholinesterase (Gen Bank: AAA68151.1) is 614 amino acids in length, and is provided herein as SEQ ID No:1, as follows:

```
                                         [SEQ ID No: 1]
  1  mrppqcllht  pslaspllll  llwllgggvg aegredaell  vtvrggrlrg  irlktpggpv 61  saflgipfae  ppmgprrflp  pepkqpwsgv vdattfqsvc  yqyvdtlypg  fegtemwnpn 121  relsedclyl  nvwtpyprpt  sptpvlwiy gggfysgass  ldvydgrflv  qaertvlvsm 181  nyrvgafgfl  alpgsreapg  nvglldqrla lqwvqenvaa  fggdptsvtl  fgesagaasv 241  gmhllsppsr  glfhravlqs  gapngpwatv gmgearrrat  qlahlvgcpp  ggtggndtel 301  vaclrtrpaq  vlvnhewhvl  pqesvfrfsf vpvvdgdfls  dtpealinag  dfhglqvlvg 361  vvkdegsyfl  vygapgfskd  neslisraef lagvrvgvpq  vsdlaaeavv  lhytdwlhpe 421  dparlreals  dvvgdhnvvc  pvaqlagrla aqgarvyayv  fehrastlsw  plwmgvphgy 481  eiefifgipl  dpsrnytaee  kifaqrlmry wanfartgdp  neprdpkapq  wppytagaqq 541  yvsldlrple  vrrglraqac  afwnrflpkl lsatdtldea  erqwkaefhr  wssymvhwkn 601  qfdhyskqdr  csdl
```

It will be appreciated that the first 31 amino acid residues of SEQ ID No:1 are removed while the protein is released, thereby leaving a 583 amino acid sequence. Accordingly, it is preferred that the cyclic polypeptide, derivative or analogue thereof comprises an amino acid sequence derived from the C-terminus of acetylcholinesterase, or a truncation thereof, wherein the acetylcholinesterase comprises an amino acid sequence substantially as set out in SEQ ID No:1, preferably excluding the 31 amino acids at the N-terminal.

Preferably, the cyclic polypeptide, derivative or analogue thereof comprises an amino acid sequence derived from the last 300, 200, 100 or 50 amino acids forming the C-terminus of acetylcholinesterase, or a truncation thereof, preferably wherein the acetylcholinesterase comprises an amino acid sequence substantially as set out in SEQ ID No:1. The cyclic polypeptide, derivative or analogue thereof preferably comprises an amino acid sequence derived from the last 40 amino acids forming the C-terminus of acetylcholinesterase, or a truncation thereof.

Preferably, the cyclic polypeptide, derivative or analogue thereof comprises between 8 and 40 amino acid residues, more preferably between 10 and 30 amino acids, and most preferably between 12 and 20 amino acids. As shown in FIG. 11, the inventor has prepared a sequence alignment between β-amyloid (Aβ), and three peptides that are derived from the C-terminus of AChE, which are referred to herein as T30, T14 and T15. The amino acid sequence of part of β-amyloid (Aβ) is provided herein as SEQ ID No:2, as follows:—

[SEQ ID No: 2]
DAEFRHDSGYEVHHQKLVFFAEDVGSNKGAIIGLMVGGVVIA

The amino acid sequence of T30 (which corresponds to the last 30 amino acid residues of SEQ ID No:1) is provided herein as SEQ ID No:3, as follows:—

[SEQ ID No: 3]
KAEFHRWSSYMVHWKNQFDHYSKQDRCSDL

The amino acid sequence of T14 (which corresponds to the 14 amino acid residues located towards the end of SEQ ID No:1, and lacks the final 15 amino acids found in T30) is provided herein as SEQ ID No:4, as follows:

[SEQ ID No: 4]
AEFHRWSSYMVHWK

The amino acid sequence of T15 (which corresponds to the last 15 amino acid residues of SEQ ID No:11 is provided herein as SEO ID No:5, as follows:—

[SEQ ID No: 5]
NQFDHYSKQDRCSDL

The inventor has generated a consensus sequence based on SEQ ID No's 2-5, which is provided herein as SEQ ID No:6, as follows:—

[SEQ ID No: 6]
AEFx$_1$x$_2$x$_3$Sx$_4$Yx$_5$VH

Preferably, in SEQ ID No:6, x$_1$ can be a basic amino acid residue, preferably histidine (H); x$_2$ can be a basic amino acid residue, preferably arginine (R); x$_3$ can be an aromatic amino acid residue, preferably tryptophan (W); x$_4$ can be an amino acid residue having an aliphatic hydroxyl side chain, preferably serine (S); x$_5$ can be tryptophan (W) or methionine (M).

It will be appreciated that any of the sequences represented as SEQ ID No:2-6 can be readily cyclated to form a cyclic polypeptide of the first aspect. For example, cyclization of peptides can be achieved by sidechain-to-sidechain, sidechain-to-backbone, or head-to-tail (C-terminus to N-terminus) cyclization techniques. In one preferred embodiment, head-to-tail cyclization is the preferred method by which the cyclic polypeptides are produced. The cyclic polypeptides may be synthesised using either classical solution-phase linear peptide cyclization or resin-based cyclization. Preferred methods for cyclization are described in the Examples. In another preferred embodiment, the polypeptide is produced using a cyclization cleavage approach, in which the cyclic polypeptide is synthesized by cyclization after step-wise linear peptide synthesis. An advantage of this method is that the sidechain does not need to be anchored, making the approach more general. Preferably, prior to use, resultant samples of cyclic peptides can be analysed by MALDI-TOF MS.

Accordingly, a preferred polypeptide according to the invention comprises cyclic SEQ ID No:3, 4, 5 or 6, or a functional variant or fragment thereof.

In one embodiment, the cyclic polypeptide comprises the amino acid sequence of SEQ ID No:3, and the N-terminal lysine residue is linked to the C-terminal leucine residue to form a circular chain of amino acids. In another embodiment, the cyclic polypeptide comprises the amino acid sequence of SEQ ID No:4, and the N-terminal alanine residue is linked to the C-terminal lysine residue. In yet another embodiment, the cyclic polypeptide comprises the amino acid sequence of SEQ ID No:5, and the N-terminal asparagine residue is linked to the C-terminal leucine residue. In another embodiment, the cyclic polypeptide comprises the amino acid sequence of SEQ ID No:6, wherein $x_1$ can be a basic amino acid residue, preferably histidine (H); $x_2$ can be a basic amino acid residue, preferably arginine (R); $x_3$ can be an aromatic amino acid residue, preferably tryptophan (W); $x_4$ can be an amino acid residue having an aliphatic hydroxyl side chain, preferably serine (S); $x_5$ can be tryptophan (W) or methionine (M), and the N-terminal alanine residue is linked to the C-terminal histidine residue.

The inventor found that cyclated SEQ ID No: 4 (i.e. referred to herein as "cyclated T14", "CT14" or "NBP14") surprisingly acts as a true antagonist of the α7 nicotinic-receptor, i.e. that cyclated SEQ ID No:4 protects cells from linear T14, T30 and β-amyloid toxicity. Moreover, cyclated T14 blocks compensatory AChE release induced by this toxicity of linear T14 and T30. In addition, they observed that cyclic T14 given alone has no significant effects on $Ca^{2+}$ concentrations in rat brain slices, but blocks the effects of β-amyloid. Accordingly, a preferred cyclic polypeptide of the first aspect comprises cyclic SEQ ID No:4, or a functional variant or fragment thereof.

The skilled person would appreciate that functional variants and analogues retain substantially the same biological activity as cyclic T14 in any of the experiments described in the Examples. Accordingly, a functional variant or analogue may be selected on the basis of its antagonistic activity at the Ivermectin-sensitive allosteric site on the α7 nicotinic-receptor, or by the extent to which it blocks AChE release, or the extent to which it protects cells from linear T14, T30 and β-amyloid toxicity, or the extent to which it modulates $Ca^{2+}$ levels in a rat brain slice.

The inventor is of the firm view that observed receptor antagonism provided by cyclation of the polypeptide, derivative or analogue thereof according to the first aspect was so surprising that it could never have been obvious to the skilled person. As such, the inventor believes that cyclation of any polypeptide could be used for antagonising a receptor, such as the α7 nicotinic-receptor.

Hence, in a second aspect, there is provided a receptor antagonist comprising a cyclic polypeptide, derivative or analogue thereof.

Furthermore, in a third aspect, there is provided a cyclic polypeptide, derivative or analogue thereof, for use as a receptor antagonist.

As discussed above, the inventors have surprisingly shown that the cyclic polypeptides of the invention act as an inert allosteric modulator of the α7 nicotinic-receptor which antagonises the action of T30 and amyloid beta peptides.

Hence, in a fourth aspect, there is provided a receptor allosteric modulator comprising a cyclic polypeptide, derivative or analogue thereof.

In a fifth aspect, there is provided a cyclic polypeptide, derivative or analogue thereof, for use as a receptor allosteric modulator.

The cyclic polypeptide, derivative or analogue thereof is preferably the polypeptide, derivative or analogue thereof according to the first aspect. The receptor, which the cyclic polypeptide, derivative or analogue thereof agent antagonises or allosterically modulates, may be any receptor, but is preferably an α7 receptor. Preferably, however, the receptor, which the cyclic polypeptide, derivative or analogue thereof antagonises or allosterically modulates, is the α7 nicotinic-receptor. It is preferred that the cyclic polypeptide, derivative or analogue thereof antagonises or modulates an allosteric site on the receptor, and preferably an Ivermectin-sensitive allosteric site of the receptor.

The inventors believe that they are the first to have shown that a cyclic polypeptide can be used in therapy, for example in the treatment of neurodegenerative disorders, such as Alzheimer's disease.

Thus, in a further aspect, there is provided a cyclic polypeptide, derivative or analogue thereof, for use in therapy or diagnosis.

In a further aspect, there is provided a cyclic polypeptide, derivative or analogue thereof, for use in treating, ameliorating or preventing a neurodegenerative disorder.

In yet another aspect, there is provided a method of treating, ameliorating or preventing a neurodegenerative disorder in a subject, the method comprising, administering to a subject in need of such treatment, a therapeutically effective amount of a cyclic polypeptide, derivative or analogue thereof.

As discussed above, the inventor believes that the cyclic polypeptide, derivative or analogue thereof or the receptor antagonist or allosteric modulator described herein can be used to form the basis for treating neurodegenerative disorders.

Thus, in a sixth aspect of the invention, there is provided the cyclic polypeptide, derivative or analogue thereof according to the first aspect, or the receptor antagonist according to the second aspect, or the receptor allosteric modulator of the fourth aspect, for use in therapy or diagnosis.

In a seventh aspect, there is provided the cyclic polypeptide, derivative or analogue thereof according to the first aspect, or the receptor antagonist according to the second aspect, or the receptor allosteric modulator of the fourth aspect, for use in treating, ameliorating or preventing a neurodegenerative disorder.

In a eighth aspect, there is provided a method of treating, ameliorating or preventing a neurodegenerative disorder in a subject, the method comprising, administering to a subject in need of such treatment, a therapeutically effective amount of the cyclic polypeptide, derivative or analogue thereof according to the first aspect, or the receptor antagonist according to the second aspect, or the receptor allosteric modulator of the fourth aspect.

Preferably, the neurodegenerative disorder is selected from a group consisting of Alzheimer's disease; Parkinson's disease; Huntington's disease; Motor Neurone disease; Spinocerebellar type 1, type 2, and type 3; Amyotrophic Lateral Sclerosis (ALS); and Frontotemporal Dementia, and is preferably Alzheimer's disease.

The neurodegenerative disorder which is treated is preferably one each is characterised by the damage or death of 'Global' neurons. For example, the neurodegenerative disorder may be selected from a group consisting of Alzheimer's disease; Parkinson's disease; Huntington's disease; Motor Neurone disease; Spinocerebellar type 1, type 2, and type 3; Amyotrophic Lateral Sclerosis (ALS); Frontotemporal Dementia; and Schizophrenia.

Preferably, the neurodegenerative disorder, which is treated, is Alzheimer's disease, Parkinson's disease, or Motor Neurone disease. Most preferably, the neurodegenerative disorder, which is treated, is Alzheimer's disease.

It will be appreciated that the cyclic polypeptide or receptor antagonist or the receptor allosteric modulator according to the invention may be used in a medicament which may be used in a monotherapy (i.e. use of the cyclic polypeptide, derivative or analogue thereof), for treating, ameliorating, or preventing neurodegenerative disorder, such as Alzheimer's disease. Alternatively, the cyclic polypeptide or receptor antagonist or the receptor allosteric modulator according to the invention may be used as an adjunct to, or in combination with, known therapies for treating, ameliorating, or preventing Alzheimer's disease, such as other acetylcholinesterase inhibitors.

The cyclic polypeptide according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the cyclic polypeptide across the blood-brain barrier.

It will be appreciated that the efficiency of any treatment for brain disorders depends on the ability of the candidate therapeutic compound to cross the blood-brain barrier (BBB). The inventor believes that peptides of the size of Cyclic T14 may not gain ready access following oral administration. However, it is well-known that, during Alzheimer's disease, the blood-brain barrier increases in permeability that could allow Cyclic T14 to reach the central nervous system, indeed ideally only at the sites of degeneration where it is needed, i.e. where the BBB is compromised.

Two main strategies may be applied to cross the BBB with a large molecule, such as Cylic T14 (i.e. NBP-14), including: (i) use of nanoparticules as transporters to specifically target the brain and deliver the active compound. This method has successfully been used to deliver peptides, proteins and anticancer drugs deliver to the brain; (2) use of cargo peptides. The addition of such a peptide specifically transported across the BBB allows the transfer of the cyclic peptide through a facilitated manner.

Medicaments comprising cyclic polypeptides according to the invention may be used in a number of ways. For instance, oral administration may be required, in which case the cyclic polypeptide may be contained within a composition that may, for example, be ingested orally in the form of a tablet, capsule or liquid. An alternative option for administrating Cyclic T14 (i.e. NBP14) would be to use a nasal spray, since peptide administration by nasal spray reaches the brain faster and more efficiently than oral or intravenous ways of administration (see http://memoryzine.com/2010/07/26/nose-sprays-cross-blood-brain-barrier-faster-and-safer/). Hence, compositions comprising cyclic polypeptides of the invention may be administered by inhalation (e.g. intranasally). Compositions may also be formulated for topical use. For instance, creams or ointments may be applied to the skin, for example, adjacent the brain.

Cyclic polypeptides according to the invention may also be incorporated within a slow- or delayed-release device. Such devices may, for example, be inserted on or under the skin, and the medicament may be released over weeks or even months. The device may be located at least adjacent the treatment site, e.g. the head. Such devices may be particularly advantageous when long-term treatment with cyclic polypeptides used according to the invention is required and which would normally require frequent administration (e.g. at least daily injection).

In a preferred embodiment, medicaments according to the invention may be administered to a subject by injection into the blood stream or directly into a site requiring treatment. For example, the medicament may be injected at least adjacent the brain. Injections may be intravenous (bolus or infusion) or subcutaneous (bolus or infusion), or intradermal (bolus or infusion).

It will be appreciated that the amount of the cyclic polypeptide that is required is determined by its biological activity and bioavailability, which in turn depends on the mode of administration, the physiochemical properties of the cyclic polypeptide and whether it is being used as a monotherapy or in a combined therapy. The frequency of administration will also be influenced by the half-life of the cyclic polypeptide within the subject being treated. Optimal dosages to be administered may be determined by those skilled in the art, and will vary with the particular cyclic polypeptide in use, the strength of the pharmaceutical composition, the mode of administration, and the advancement of the neurodegenerative disease. Additional factors depending on the particular subject being treated will result in a need to adjust dosages, including subject age, weight, gender, diet, and time of administration.

Generally, a daily dose of between 0.001 µg/kg of body weight and 10 mg/kg of body weight of the cyclic polypeptide according to the invention may be used for treating, ameliorating, or preventing neurodegenerative disease, depending upon which cyclic polypeptide is used. More preferably, the daily dose is between 0.01 µg/kg of body weight and mg/kg of body weight, and most preferably between approximately 0.1 µg/kg and tong/kg body weight.

The cyclic polypeptide may be administered before, during or after onset of neurodegenerative disease. Daily doses may be given as a single administration (e.g. a single daily injection or inhalation of a nasal spray). Alternatively, the cyclic polypeptide may require administration twice or more times during a day. As an example, cyclic polypeptides may be administered as two (or more depending upon the severity of the neurodegenerative disease being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of cyclic polypeptide according to the invention to a patient without the need to administer repeated doses.

Known procedures, such as those conventionally employed by the pharmaceutical industry (e.g. in vivo experimentation, clinical trials, etc.), may be used to form specific formulations of the cyclic polypeptide according to the invention and precise therapeutic regimes (such as daily doses of the agents and the frequency of administration). The inventor believes that she is the first to suggest an anti-neurodegenerative disease composition, based on the use of a cyclic polypeptide of the invention.

Hence, in a ninth aspect of the invention, there is provided a pharmaceutical composition comprising a therapeutically effective amount of the cyclic polypeptide, derivative or analogue thereof according to the first aspect or the receptor antagonist according to the second aspect or the receptor allosteric modulator of the fourth aspect, and optionally a pharmaceutically acceptable vehicle.

The pharmaceutical composition is preferably an anti-neurodegenerative disease composition, i.e. a pharmaceutical formulation used in the therapeutic amelioration, prevention or treatment of a neurodegenerative disorder in a subject, such as Alzheimer's disease.

The invention also provides in a tenth aspect, a process for making the pharmaceutical composition according to the ninth aspect, the process comprising combining a therapeutically effective amount of the cyclic polypeptide, derivative or analogue thereof according to the first aspect or the receptor antagonist according to the second aspect or the receptor allosteric modulator of the fourth aspect, with a pharmaceutically acceptable vehicle.

The cyclic polypeptide, derivative or analogue thereof is preferably Cyclic T14 (i.e. NBP14) as disclosed herein, i.e. SEQ ID No:4.

A "subject" may be a vertebrate, mammal, or domestic animal. Hence, medicaments according to the invention may be used to treat any mammal, for example livestock (e.g. a horse), pets, or may be used in other veterinary applications. Most preferably, however, the subject is a human being.

A "therapeutically effective amount" of cyclic polypeptide is any amount which, when administered to a subject, is the amount of active agent that is needed to treat the neurodegenerative disorder condition, or produce the desired effect.

For example, the therapeutically effective amount of cyclic polypeptide used may be from about 0.001 mg to about 800 mg, and preferably from about 0.01 mg to about 500 mg. It is preferred that the amount of cyclic polypeptide is an amount from about 0.1 mg to about 100 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, coatings, or tablet-disintegrating agents. The vehicle may also be an encapsulating material. In powders, the vehicle is a finely divided solid that is in admixture with the finely divided active agents according to the invention. In tablets, the active agent (i.e. the modulator) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention (the cyclic polypeptide) may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The cyclic polypeptide may be prepared as a sterile solid composition that may be dissolved or suspended at the time of administration using sterile water, saline, or other appropriate sterile injectable medium.

The cyclic polypeptide and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The cyclic polypeptide used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Although the inventors have demonstrated the surprising therapeutic effects of the cyclic polypeptide, derivative or analogue thereof according to the first aspect, due to its antagonistic nature, they believe that it will also be useful in non-clinically related experiments designed to investigate the structure and/or function of the α7 nicotinic-receptor.

Hence, in a further aspect, there is provided use of the cyclic polypeptide, derivative or analogue thereof according to the first aspect, in an in vitro or ex vivo analytical method for investigating α7 nicotinic-receptor.

Preferably, the method comprises investigating the allosteric site of the α7 nicotinic-receptor. Preferably, the method comprises using the cyclic peptide to prevent additional influx of calcium through the α7 nicotinic-receptor. The cyclic peptide preferably acts as an antagonist and blocks the calcium ions.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/nucleotide/peptide sequence", "functional variant" and "functional fragment", can be a sequence that has at least 40% sequence identity with the amino acid/nucleotide/peptide sequences of any one of the sequences referred to herein, for example 40% identity with the sequence identified as SEQ ID No:1-6, and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=-1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as $(N/T)*100$, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula: −Sequence Identity=$(N/T)*100$.

Alternative methods for identifying similar sequences will be known to those skilled in the art. For example, a substantially similar nucleotide sequence will be encoded by a sequence which hybridizes to DNA sequences or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID No: 1-6.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE DRAWINGS

For a better understanding of the invention, and to show how embodiments of the same may be carried into effect, reference will now be made, by way of example, to the accompanying Figures, in which:—

FIG. 11 shows the amino acid sequence alignment of the peptides, T30, T15, T14 and β-amyloid (Aβ);

FIG. 12 is a diagram showing the binding sites of β-amyloid and T30 on the α7-nAChR;

FIG. 13 is a graph showing the protective effect of different concentrations of NBP-14 (5, 7, 9, 10, 20, 50, 70, 1000, 5000 nM) on Calcium influx induced by T30. The values were fitted to a non linear curve with the logarithm of the inhibitor concentrations, NBP-14, versus the response of the T30, by using GraphPad Prism;

EXAMPLES

Figure 1:
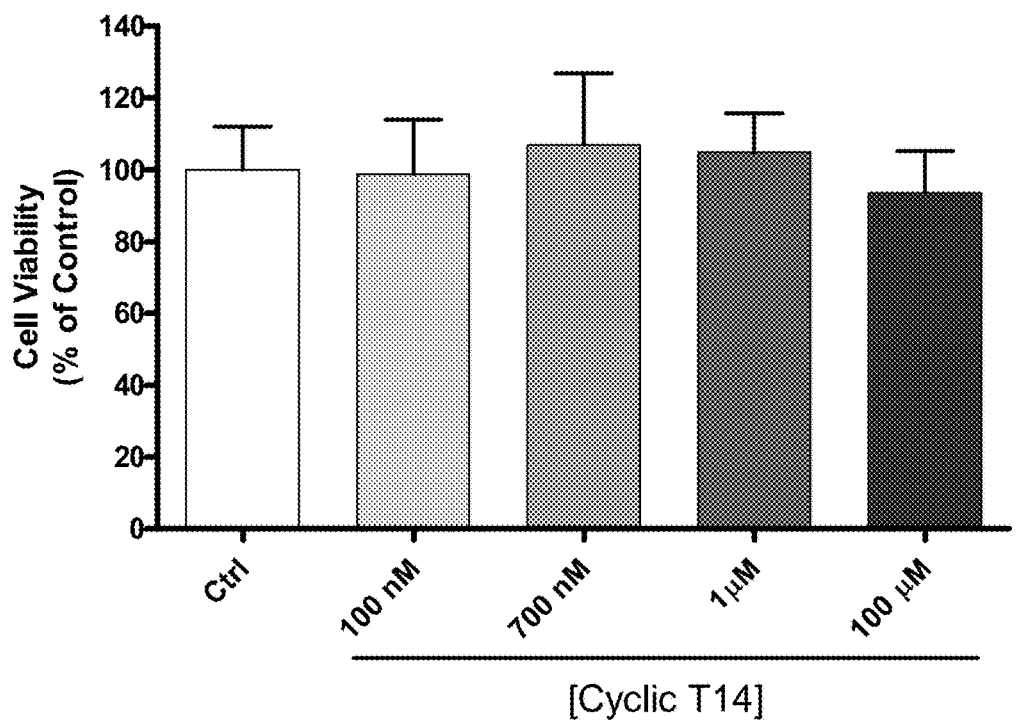
FIG. 1 is a bar chart showing no effect of Cyclic T14 alone on PC12 cell viability after 1 hour treatment. Data represent mean±SEM, N=6.

It should be noted that SEQ ID No:4 is referred to herein as "cyclated T14", "CT14" or "NBP14".

Materials and Methods

Cyclisation of Peptides

Three techniques were used to achieve cyclization of linear peptides described herein, i.e. sidechain-to-sidechain, sidechain-to-backbone, and head-to-tail (C-terminus to N-terminus) cyclization. Head-to-tail cyclization has been investigated extensively, and can involve directed Cys-Cys disulphide cyclization (up to two per molecule). Careful monitoring of the reaction ensures 100% cyclization. Two general approaches are used for synthesis: (1) classical solution-phase linear peptide cyclization under high dilution conditions; and (2) resin-based cyclization. Two distinct protocols were employed in the solid phase synthesis (1):—
- (a) The on-resin cyclization of a peptide anchored via a sidechain functional group, such as imidazole, 3 acid, 4 amine' or alcohol, was carried out. The peptide was orthogonally protected as an ester at the C-terminus, and the peptide was then assembled through regular Boc or Fmoc synthesis followed by saponification, cyclization and cleavage.
- (b) Another protocol that was used was the cyclization cleavage approach, in which the cyclic peptide was synthesized by cyclization after step-wise linear peptide synthesis. One advantage of this method is that the sidechain does not need to be anchored, making the approach more general than (a). (Christopher J. White and Andrei K. Yudin (2011) Nature Chemistry 3; Valero et al (1999) *J Peptide Res.* 53, 76-67; Lihu Yang and Greg Morriello(1999) Tetrahedron Letters 40, 8197-8200; Parvesh Wadhwani et al (2006) J. Org. Chem. 71, 55-61).

Resultant samples of cyclic peptides were analysed by MALDI-TOF MS.

PC12 Cell Culture

PC12 cells are a cloned, pheochromocytoma cell line derived from the adrenal medulla (Greene and Tischler, 1976, Proc Natl Acad Sci USA 73: 2424-2428; Mizrachi et al., 1990, Proc Natl Acad Sci USA 87: 6161-6165). They are easily cultured and readily accessible to experimental manipulations. Since chromaffin cells are derived from the neural crest but are located in the centre of an accessible peripheral organ (the adrenal medulla) they have been described as offering a 'window' into the brain (Bornstein et al., 2012, Mol Psychiatry 17: 354-358). These cells serve as a powerful, albeit novel, in vitro model for studying the still unknown primary process of neurodegeneration and the reasons why they are useful for this project are the following: the adrenal medulla in Alzheimer's patients shows various pathological features reminiscent of those seen in the CNS, e.g. numerous Lewy-body like inclusions, neurofibrillary tangles and paired helical filaments, as well as expression of amyloid precursor protein (APP) (Takeda et al., 1994, Neurosci Lett 168: 57-60). Moreover Appleyard and Macdonald (1991, Lancet 338: 1085-1086) demonstrated a selective reduction only in the soluble i.e. releasable form of AChE from the adrenal gland in AD, perhaps due to its enhanced secretion into the plasma, where it is elevated in AD patients (Atack et al., 1985, J Neurol Sci 70: 1-12; Berson et al., 2008, Brain 131: 109-119).

Wild-type PC12 cell were provided by Sigma-Aldrich (St. Louis, MO). The culture was routinely plated in 100 mm dishes (Corning) coated with collagen (2 µg/cm$^2$) and maintained in growth medium with Minimum Essential Medium Eagle (MEM) supplemented with heat-inactivated 10% horse serum (HS) and 5% foetal bovine serum (FBS), 10 mM HEPES, 2 mM L-Glutamine and 1:400 Penicillin/streptomycin solution. Cells were maintained at 37° C. in a humidified atmosphere 5% $CO_2$ and the medium was replaced every 2 days. For splitting, cells were dislodged from the dish using a pipette with medium, with a portion of these replated onto new cultured dishes. Cells were used between passages 12 and 25.

Cell Membrane Preparation

PC12 membranes where obtained to perform binding assays. PC12 cells were grown until confluence on 100 mm plates. Growth medium was removed and ice-cold 50 mM Tris-HCl buffer (pH 7.4) containing 4.5 µg/µl aprotinin and 0.1 mM phenylmethylsulphonylfluoride (PMSF) were added. Cells were mechanically detached and pelleted by centrifugation (1040×g) for 4 minutes at 4° C. Pellets were homogenized with a Polytron and centrifuged (13000×g) for 20 minutes at 4° C. The pellets were resuspended in fresh buffer and incubated at 37° C. for 10 minutes to remove endogenous neurotransmitters. The samples were subsequently re-centrifuged. The final pellet was resuspended in buffer and the protein concentration determined using the Bradford Reagent (Sigma-Aldrich, St. Louis, MO). The cell membrane preparation was stored at −80° C.

β-Amyloid Preparation

β-Amyloid (1-42) fibrils were prepared as described by provider (Abcam, Cambridge UK)). 1 mg of β-Amyloid (1-42) was dissolved in 212 µl of 1,1,1,3,3,3-hexafluoro-2-propanol (HFIP) and 10 µl of $NH_4OH$. After sonication and distribution of 10 µl of sample per tube, samples were dried in a speed vacuum drier (Thermo Fisher Scientific, Loughborough, UK) and stored at −20° C. For experiments, samples were diluted in 2 µl of DMSO (5 mM) and 98 µl of HCl (0.01 N) to ensure fibril formation and incubated over night at 37° C.

[$^3$H] Ivermectin Binding Assay

For the binding with PC12 membranes, each incubation was performed in polystyrene tube (VWR International Ltd; Leicestershire, UK) containing 0.25 ml of membranes diluted in Tris-HCl 50 mM buffer (containing 50 µg of PC12 membranes) with 5 nM [3H] Ivermectin (American Radiolabeled Chemicals, USA) in the absence or presence of different concentrations of AChE peptide T30, β-Amyloid or Cyclic T14 (0.1, 0.5, 0.7, 1, 2, 10 µM) diluted in Tris-HCl 50 mM, in a final volume of 0.5 ml for 2 h at 4° C. Thereafter, samples were filtered through Brandel GB glass fibre filters (MD, USA); pre-soaked in 0.5% polyethylenemine by a Harvester (Brandel; MD, USA). Tubes were washed 3 times with ice cold 50 mM Tris-HCl buffer. Radioactivity in the tubes was counted by scintillation spectrometry using a 300 SL Liquid scintillation counter (Lablogic Systems Limited, UK). Specific binding was determined by subtracting the non-specific (cells treated with Ivermectin 30 µM) value to all the tubes.

Cell Viability Assay

The cell viability assay used was the sulforhodamine B (SRB) colorimetric assay for toxicity screening. The day before of the experiment cells were seeded onto collagen-coated 96-well plates in a concentration of 40,000 cells/well. Cell concentration was determined by the Fuchs-Rosenthal chamber. Drugs were prepared in MEM containing L-Glutamine and cells were treated with different concentrations of Cyclic T14 (0.1-100 µM) and T30, T14 and Aβ (10 µM) alone or combined with Cyclic T14 (0.1 and 0.7 µM). After treatment, medium was replaced and cells were fixed by adding 100 µl of 10% Trichloroacetic Acid (TCA) for 1 h at 4° C. Thereafter, cells were washed with H$_2$O and stained with 100 µl of a 0.057% SRB solution in 1% Acetic acid (HAc) for 30 minutes at room temperature. After staining cells were washed with 1% HAc for removing the excess of SRB and then incubated with 200 µl of 10 mM Tris base (pH 10.5) and shake it for 5 minutes to solubilise the protein-bound dye. Measurement of the absorbance took place in a $V_{Max}$ Kinetic Microplate Reader (Molecular Devices) at 490 nm.

Acetylcholinesterase Activity Assay

AChE activity was measured using the Ellman reagent that measures the presence of thiol groups as a result of AChE activity. Cells were plated the day before the experiment as for the cell viability assay. Cells were treated with different concentrations of Cyclic T14 (0.1-100 µM) and T30, T14 and Aβ 10 µM alone or combined with Cyclic T14 (0.1 and 0.7 µM). After treatment, supernatant (perfusate) of each treatment was collected and 25 µL of each condition were added to a new flat bottomed 96 well plate followed by the addition of 175 µl of Ellman reagent (Solution A: KH$_2$PO$_4$ 139 mM and K$_2$HPO$_4$ 79.66 mM, pH 7.0; solution B (substrate): Acetylthiocholine Iodide 11.5 mM; Solution C (Reagent): 5,5'-Dithiobis (2-nitrobenzoic acid) 8 mM and NaHCO$_3$ 15 mM). The Ellman reagent was prepared as a mixture of the 3 solutions in a ratio 33(A):3(B):4(C). Absorbance measurements were taken at regular intervals (3, 10, 30 and 60 mins) across experiments at 405 nm.

Calcium Fluorometry

Increases in intracellular Ca$^{2+}$ were monitored by measuring changes in fluorescence in cells loaded with Fluo-4 (Life Technologies Corporation, UK). The brain slices were incubated for 2 hours in 124 mM NaCl, 3.7 mM KCl, 26 mM NaHCO$_3$, 2 mM CaCl$_2$, 1.3 mM MgSO$_4$, 1.3 mM KH2PO$_4$ and 10 mM glucose; pH: 7.1 containing β-Amyloid, CyclicT14 or β-Amyloid+Cyclic T14. After the 2 hours, slices were incubated in the dark for 40 minutes at room temperature with 1.2 ml/well of loading medium that contained: Tyrode's salt solution (TSS; 137 mM NaCl, 2.7 mM KCl, 1.0 mM MgCl$_2$, 2.5 mM CaCl$_2$, 0.2 mM NaH$_2$PO$_4$, 12.0 NaHCO$_3$, 5.5 glucose, pH 7.4), Fluo-4 (2 µM), Pluronic F127 (0.02%) and probenecid (2 mM). Probenecid is a blocker of the multidrug resistant protein, an ion transporter, and avoids the excretion of the fluorescent molecule from the cell. After incubation, slices were washed with TSS and 1200 µl/well of de-esterification medium, containing TSS and probenecid, were added. Slices were incubated in the dark for 20 minutes at 22° C. Fluorescence measurements (excitation 485 nm, emission 538 nm) were recorded in a Fluostar Optima (BMG, UK) plate reader.

Drugs and Reagents

MEM, culture serums, antibiotics, collagen, sulforhodamine B, Ivermectin and buffers reagents were provided by Sigma-Aldrich (St. Louis, MO). T30, T14 AChE peptides and Cyclic T14 were synthesized by Genosphere Biotechnologies (France). Stocks of peptides were diluted in distilled water.

Data Analysis

In each of the different techniques, the statistics analysis was performed with the average of the percentage values of 12 or more experiments. Comparisons between multiple treatment groups and the same control were performed by one-way analysis of variance (ANOVA) and Tukey's post-hoc tests using GraphPAD Instat (GraphPAD software, San Diego, CA). These tests compare the means of every treatment to the means of every other treatment; that is, apply simultaneously to the set of all pairwise comparisons and identify where the difference between two means is greater than the standard error would be expected to allow. Statistical significance was taken at a P value <0.05. Graphs were plotted using GraphPAD Prism 6 (GraphPAD software, San Diego, CA). In the case of the binding experiment, results were obtained as counts per minute (cpm) and transformed to percentages related to control. Results were fitted to a model of one site competition binding using GraphPad Prism. In the case of the calcium results, the EC$_{50}$ values were calculated by fitting the logarithm of the experimental data points to a single site Hill equation using a non-linear regression curve using GraphPad Prism.

Example 1—Cyclisation of T14

The inventor synthesised an agent that selectively targets the allosteric site on the α7 nicotinic acetylcholine receptor, to compete for binding with T14/T30 and also to antagonise β-amyloid. The agent is a cyclic form of T14 having the amino acid sequence: AEFHRWSSYMVHWK [SEQ ID No:4], with the N-terminal alanine residue being connected to the C-terminal lysine residue. Genosphere Biotechnologies (France) performed the cyclisation of T14 by transforming the linear peptide into an N-terminal to C-terminal lactam. The following examples demonstrate for the first time how the Cyclic T14 peptide blocks the established toxic effects of the T30 peptide and amyloid in vitro.

Example 2—Cyclic T14 is not Toxic when Applied Alone

Using sulforhodamine B (SRB) as a cell viability detection method, PC12 cells were treated for 1 hour with Cyclic T14 produced in example 1. As a result, no changes in cell viability were observed suggesting no toxicity at concentrations as high as 100 µM (100 nM: 98.76±15.15; 700 nM: 106.94±19.92; 1 µM: 104.82±10.9; 100 µM: 93.58±11.62) (see FIG. 1).

Example 3—Cyclic T14 does not Affect AChE Enzymatic Activity

Figure 2:
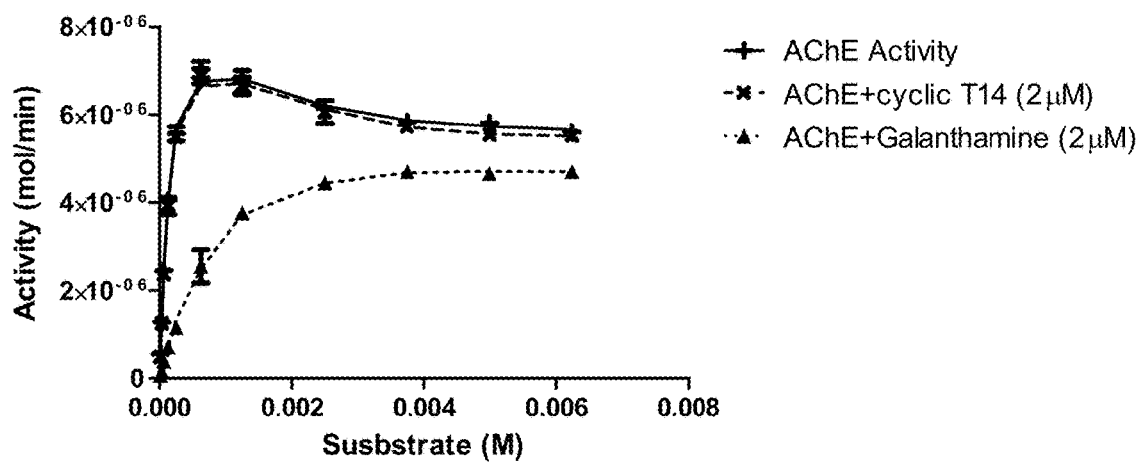
FIG. 2 is a graph showing no change in enzymatic activity of AChE (determined by its ability to cleave increasing concentrations of a substrate) in the presence or absence of Cyclic T14. In contrast, Galanthamine displays highly significant competitive inhibition of enzyme activity. Data represent mean±SD, N=4.

The inventor next decided to confirm whether or not Cyclic T14 affects the enzymatic activity of acetylcholinesterase (AChE). AChE enzymatic activity was measured using the acetylcholinesterase activity assay. The inventor found that the presence of Cyclic T14 (2 µM) did not affect enzyme activity of acetylcholinesterase: in contrast Galanthamine (2 µM) was strongly inhibitory (see FIG. 2).

Figure 3:
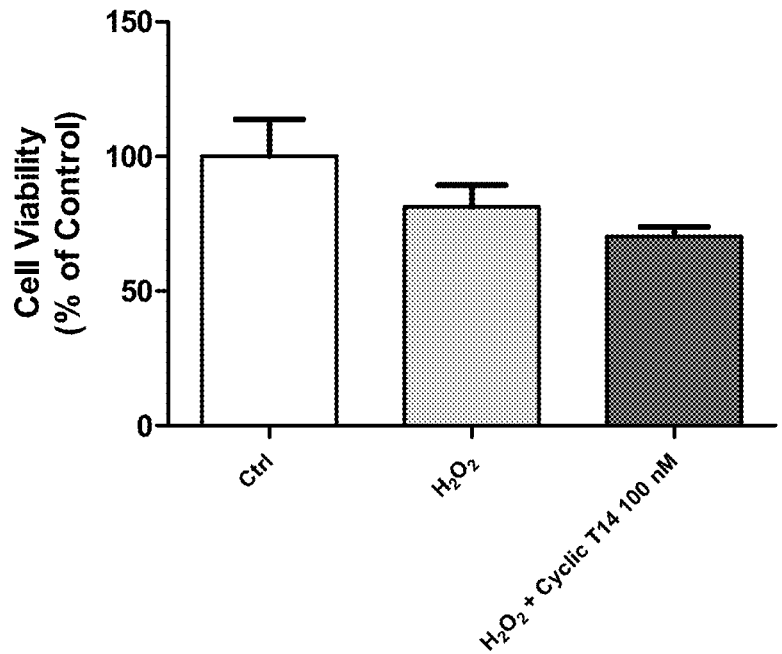
FIG. 3 is a bar chart showing the non-specific toxic effect of $H_2O_2$ (100 µM) alone, and its persistence when combined with Cyclic T14 (100 nM) on cell viability. Data represent mean±SEM, N=6. * vs Control; *P<0.05, **P<0.01.

Example 4—Cyclic T14 does not Protect Against Non-Specific Toxicity of Hydrogen Peroxide The inventors then determined whether or not Cyclic T14 protects PC 12 cells against the non-specific cytotoxic effects of the hydrogen peroxide. As can be seen in FIG. 3, there is no significant difference when H$_2$O$_2$ is given alone or in combination with Cyclic T14.

Example 5—Cyclic T14 Protects Cells from T14, T30 and β-Amyloid Toxicity

Figure 4A:
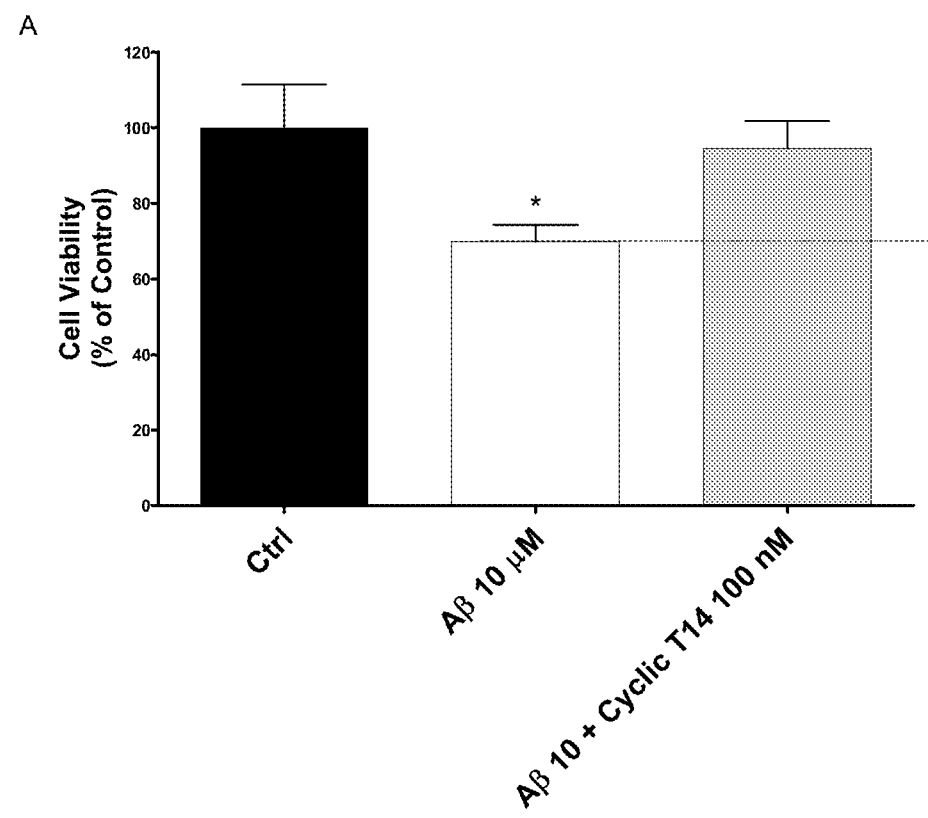
FIGS. 4A-4C show the effect after 1 hour treatment of (A) β-Amyloid (10 µM), (B) T14 (10 µM) and (C) T30 (10 µM) alone, and combined at time zero with Cyclic T14 (100 nM). Data represent mean±SEM, N=12. * vs Control; *P<0.05, ***P<0.001.
Figure 4B:
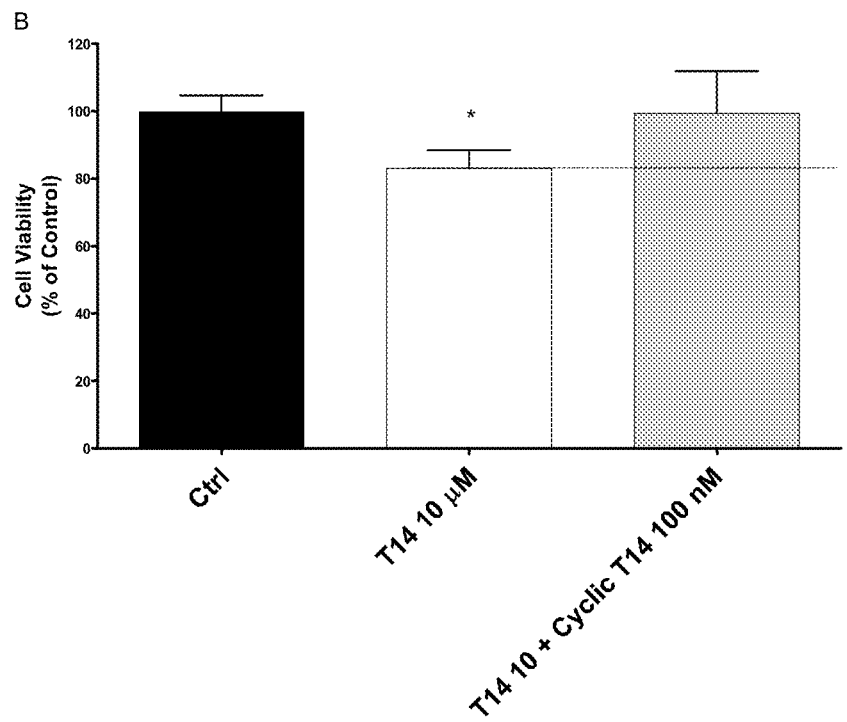
Figure 4C:
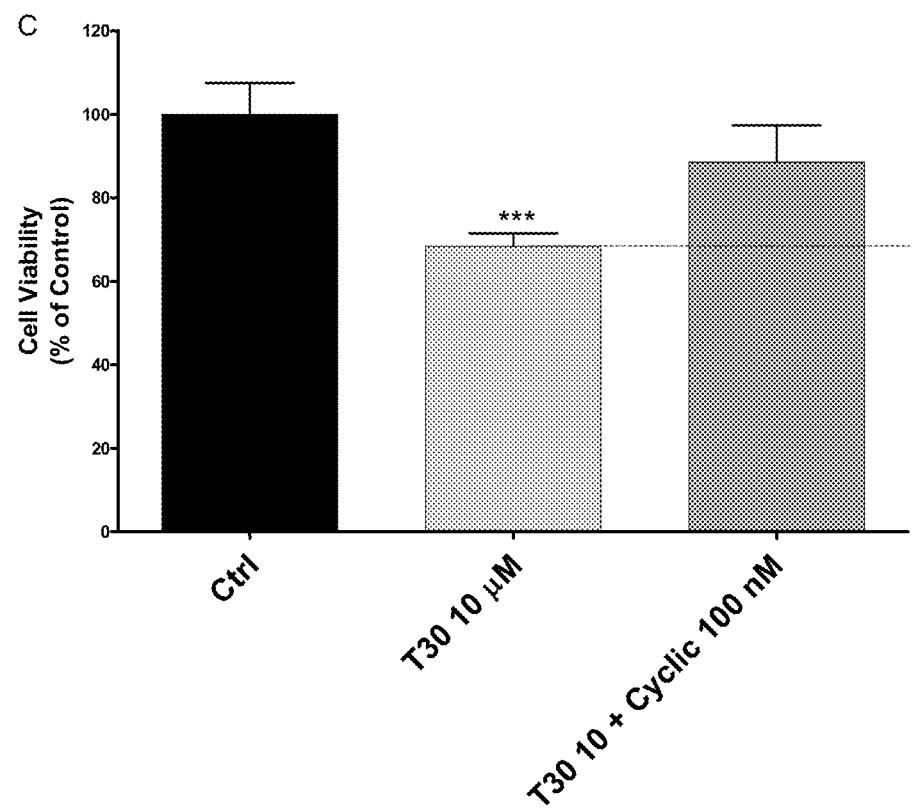

Using SRB as a cell viability detection method, PC12 cells were treated for 1 hour with (4A) β-amyloid, (4B) linear T14, or (4C) T30, either alone or combined with Cyclic T14 (100 nM). As shown in FIGS. 4A-4C, the three peptides alone induce a decrease in cell viability (Aβ: 69.875±4.38; T14: 83.02±5.385 and T30: 68.395±3.095), but when combined with Cyclic T14 cells were surprisingly protected from death (A(β+C14: 94.475±7.4; T14+C14: 99.4±$^{12}$0.475; T30+C14: 88.59±8.785).

Example 6—Cyclic T14 Blocks AChE Release Induced by T14 and T30

Figure 5:
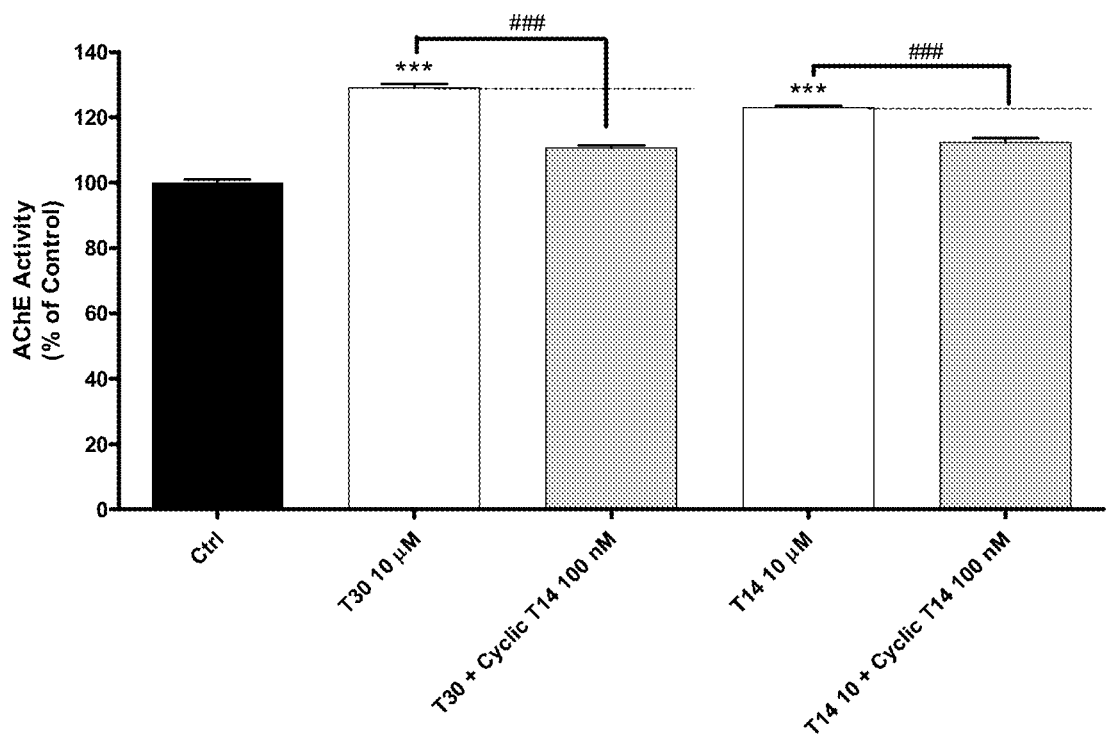
FIG. 5 is a bar chart showing AChE activity after treatment of PC12 cells with T30 (10 µM) alone, T14 (10 µM) alone or combined with Cyclic T14 (100 nM). Data represent mean±SEM, N=6. * vs Control, ***P<0.001; # within groups, ####P<0.001.

The colourmetric Ellman assay was used to assess AChE activity as a compensatory response after a toxic stimulus. Cells were treated for 1 hour with linear T14 and T30 (10 μM) alone and combined with Cyclic T14 (100 nM) (see FIG. 5). All the peptides induce an increase of AChE activity (T30: 129.10±1.18; T14: 123.0 t 0.62) that was partially blocked when combined with the Cyclic T14 (T30+C14: 110.58 t 0.80; T14+C14: 112.30±1.39).

Example 7—β-Amyloid, T30 and T14 Displace [3H] Ivermectin Binding

Figure 6:
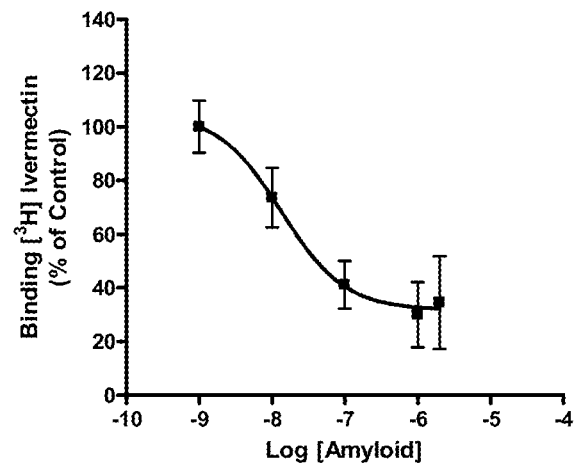
FIG. 6 shows competition curves of the inhibition of [$^3$H] Ivermectin binding by β-Amyloid, T30 and T14 in membranes of PC12 cells, as also shown in rat brain membranes. Data represent the means±SEM, N=3.
Figure 6:
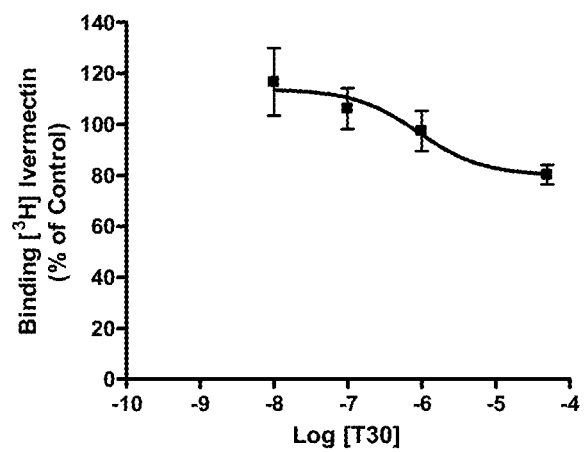
Figure 6:
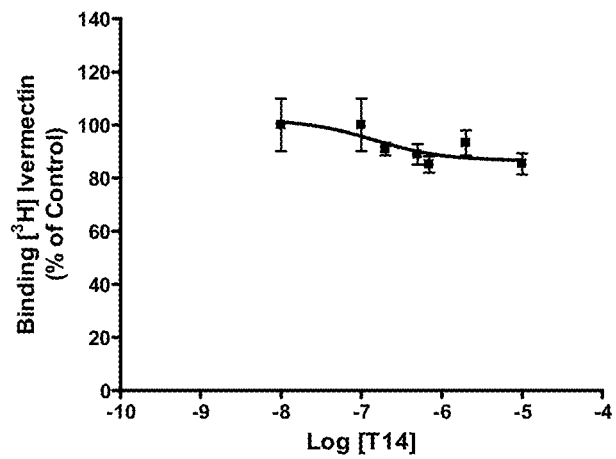

In order to demonstrate that the α7nAChR (the α7 nicotinic acetylcholine receptor) is a target for the β-Amyloid, T30 and T14 in the preparations used here. [3H] Ivermectin binding assays were performed on PC12 cell membrane and demonstrate in a log dose-response manner a decrease of the affinity of the allosteric site of the receptor where the ligand [$^3$H] Ivermectin binds (see Table 1, FIG. 6).

TABLE 1

Data showing the percentage of [$^3$I-1] Ivermectin binding on PC12 cells in the resence of differelicentratiolisof-Aillyloid, T30 and T14, N = 2.

| % [$^3$11] Ivermectin (Mean ± SEM) | β-Amyloid | T30 | T14 |
|---|---|---|---|
| 1 nM | 100.00 ± 9.70 | 109.16 ± 11.9 | 100 ± 9.91 |
| 10 nM | 73.61 ± 11.12 | 116.63 ± 13.25 | 90.92 ± 2.38 |
| 100 nM | 41.17 ± 8.90 | 106.15 ± 8.04 | 88.92 ± 3.82 |
| 1 μM | 29.98 ± 12.20 | 97.41 ± 7.9 | 85.17 ± 3.03 |
| 5 μM | 34.49 ± 17.29 | 80.22 ± 3.81 | 85.36 ± 3.96 |

Example 8—Cyclic T14 Displaces [3H] Ivermectin Binding with Greater Efficacy than Galanthamine Low micromolar concentrations of cyclic T14 displaced [$^3$H] Ivermectin with similar affinity but with significantly greater efficacy than Galanthamine.

TABLE 2

Data showing the percentage of [$^3$H] Ivermectin binding on PC12 cells in the presence of different concentrations of Cyclic T14 and Galanthamine, N = 6

| % [$^3$H] Ivermectin (Mean ± SEM) | Cyclic T14 | Galanthamine |
|---|---|---|
| 100 nM | 98.10 ± 3.28 | 100.00 ± 11.48 |
| 200 nM | 80.81 ± 4.37 | 97.86 ± 1.40 |

TABLE 2-continued

Data showing the percentage of [$^3$H] Ivermectin binding on PC12 cells in the presence of different concentrations of Cyclic T14 and Galanthamine, N = 6

| % [$^3$H] Ivermectin (Mean ± SEM) | Cyclic T14 | Galanthamine |
|---|---|---|
| 500 nM | 79.72 ± 6.76 | 90.96 ± 1.87 |
| 700 nM | 62.26 ± 17.63 | 69.68 ± 9.87 |
| 1 μM | 29.006 ± 8.23 | 67.17 ± 6.64 |
| 2 μM | 13.46 ± 10.40 | 66.32 ± 4.29 |

Figure 8:
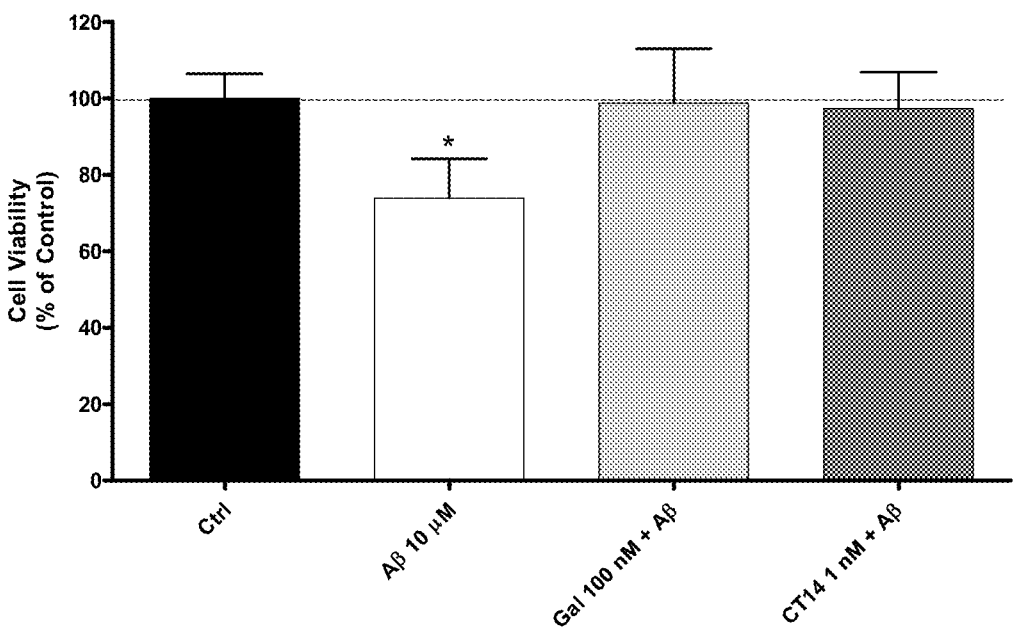
FIG. 8 is a bar chart showing the minimum effective concentration of Galanthamine (100 nM) and Cyclic T14 (1 nM) against β-Amyloid (10 µM) on cell viability. Data represents mean±SEM, N=6. * vs Control; *P<0.05.

Example 9—Cyclic T14 Protects Cells from γ-Amyloid Toxicity with Greater Efficacy than Galanthamine Using SRB as a cell viability detection method, PC12 cells were treated for 1 hour with β-amyloid either alone or combined with Cyclic T14 (1 nM) or Galanthamine (moo nM). As shown in FIG. 8, Cyclic T14 protected against Aβ toxicity (97.34±9.57) in a dose two orders of magnitude lower than Galanthamine (98.79±14.21).

Figure 9:
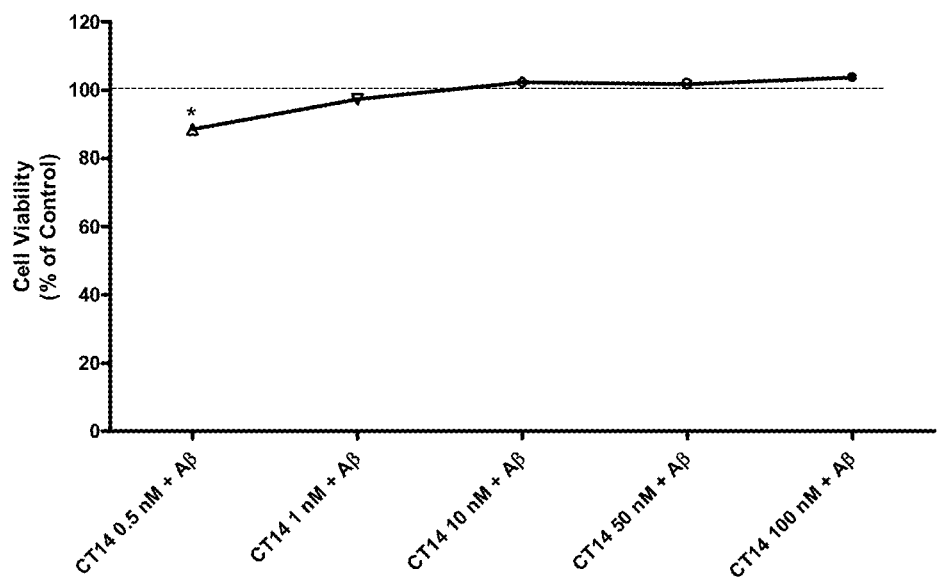
FIG. 9 is a graph showing the dose response effect of Cyclic T14 (1 nM) against β-Amyloid (10 µM) on cell viability. Data represents mean±SEM, N=6. * vs Control; * P<0.05.

Example 10—Minimum Concentration of Cyclic T14 Required for 100% Protection Against β-Amyloid Using SRB as a cell viability detection method, PC12 cells were treated for 1 hour with β-amyloid combined with Cyclic T14 in concentrations increasing from 0.5 nM to 100 nM (0.5: 88.49±10; 1: 97.34±9.57; 10: 102.28±8.53; 50: 101.79±13.99; moo: 103.68±6.34). The threshold dose for full protection was 1 nM (FIG. 9).

Example 11—Cyclic T14 Reduces $Ca^{2+}$ Levels in Rat Brain Slices

Fluorometry was used to detect variations in calcium levels after treatment for two hours with Cyclic T14 1 μM, β-Amyloid 10 μM and both combined. Cyclic T14 does not change the basal level of intracellular calcium whilst β-Amyloid induces to increase the intracellular calcium level, which is returned to baseline by Cyclic T14 (see FIG. 10).

Example 12—T30 Exhibits a High Binding Affinity for the Allosteric Site of the α7 Nicotinic-Receptor Using tests for viability, the inventor has shown that T30 has a binding affinity approximately three orders of magnitude higher (5 nM) for the allosteric site on the α7 nicotinic-receptor, than drugs currently in clinical use, e.g. galanthamine (10 μM).

General Discussion

Cyclic T14 is a novel α7 nicotinic-receptor inert allosteric modulator of the α7 nicotinic-receptor which antagonises the action of $T_{30}$ and amyloid beta peptides Cyclic T14 is a novel α7 nicotinic-receptor antagonist. The inefficacy of protection against the non-specific agent hydrogen peroxide suggests that the blocking action of Cyclic T14 is selective and receptor mediated. Cyclic T14 antagonises the toxic effects of T30 in a variety of tests indicating that it prevents the additional influx of calcium through an allosteric site on the α7 receptor by competing for binding with T30 as well as with amyloid. The enhanced stability of cyclic peptides would account for this effective displacement.

Why would a Cyclic T14-Based Drug be More Effective than Currently Available Treatments?

Figure 7:
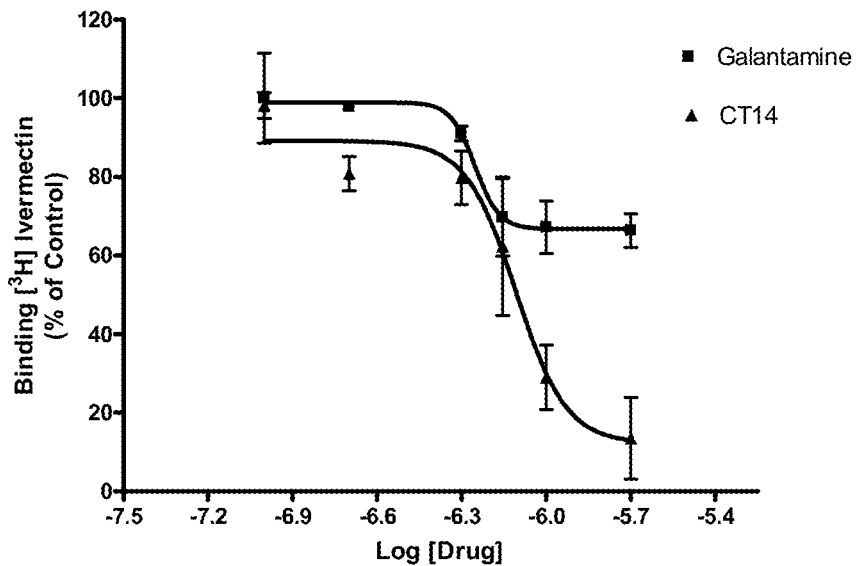
FIG. 7 shows competition curves of the inhibition of [$^3$H] Ivermectin binding by Cyclic T14 and Galanthamine in membranes of PC12 cells, as also shown in rat brain membranes. Data represent the means±SEM, N=6.

The inventor has recently shown that T30 has a binding affinity approximately three orders of magnitude higher (5 nM) for the allosteric site on the α7 receptor, than drugs currently in clinical use, e.g. galanthamine (10 μM). Indeed, this observation would suggest the reason why such drugs currently being prescribed have proved relatively disappointing (See Table 1; Kramp & Herrling, 2011, Neurodegenerative Dis 8, 44-94): if endogenous T30, in excess in the Alzheimer patient's brain, is already occupying the key site, it will not be displaced by low-affinity competition. However, it would be blocked by an agent with very similar or indeed superior binding affinities, as suggested here (see FIG. 7). Such an agent has therefore the potential for being a highly effective drug.

A further advantage of the Cyclic T14 is that, unlike galanthamine, which is additionally an AChE inhibitor, it would have no other biological actions, other than to bind to the receptor. If, as the inventor's previous work suggests (Greenfield, 2013, Chem Biol Interact. 203(3)543-6), T30 is indeed the pivotal signalling molecule in neurodegenerative diseases, then its antagonism would be combatting these diseases at the most fundamental and specific level. In any event, the observation that this novel agent also antagonises amyloid would be of great clinical interest, where amyloid is implicated in the degenerative process, irrespective of its precise role. It should be noted that whilst other therapeutic candidates targeting the availability of β-Amyloid (e.g. gamma secretase inhibitors) have been ineffective, this is the first instance, of the effective blockade of amyloid toxicity.

TABLE 3

Comparison of features of Galanthamine vs Cyclic T14-based drug

| Galanthamine | Dream Drug | Cyclic T14 |
|---|---|---|
| Inhibits AChE (side effects) | Does not affect AChE activity | ✓ |
| Known action at various receptors | Specific action at α7 receptor | ✓ |
| Micromolar affinity | Nanomolar affinity | ✓ |
| Blocks β-Amyloid at high doses (0.1 μM) | Blocks β-Amyloid at low doses 1 nM) | ✓ |
| Low permeability CNS | Should have high permeability CNS | |
| High bioavailability periphery (Side effects as diarrhoea) | Should have low peripheral bioavailability | |
| Post-symptomatic | Pre-symptomatic | |

The inventor believes that the current results suggest that the conformation of Cyclic T14 allows it to bind to its specific target, α7 nicotinic-receptor. Referring to FIG. 12, there is shown a schematic diagram of the α7 nicotinic-receptor. The homomeric receptor contains five identical α7 subunits, which are each symmetrically arranged around a central pore through which ions, such as $Na^+$ and $Ca^{2+}$, pass when the receptor is activated. Each α7 subunit contains an orthosteric binding site (i.e. the active site) and an allosteric binding site. Normal physiological activation of the receptor is achieved by the binding of a single acetylcholine molecule to the interface of two α7 subunits via each of their orthosteric sites. Other known ligands of the orthosteric site include (but are not limited to) choline and Methyllycaconitine (MLA). Ligands of the allosteric site include (but are not limited to) linear and cyclical T14, cyclical and linear T30, galantamine, ivermectin and PNU12.

Figure 10:
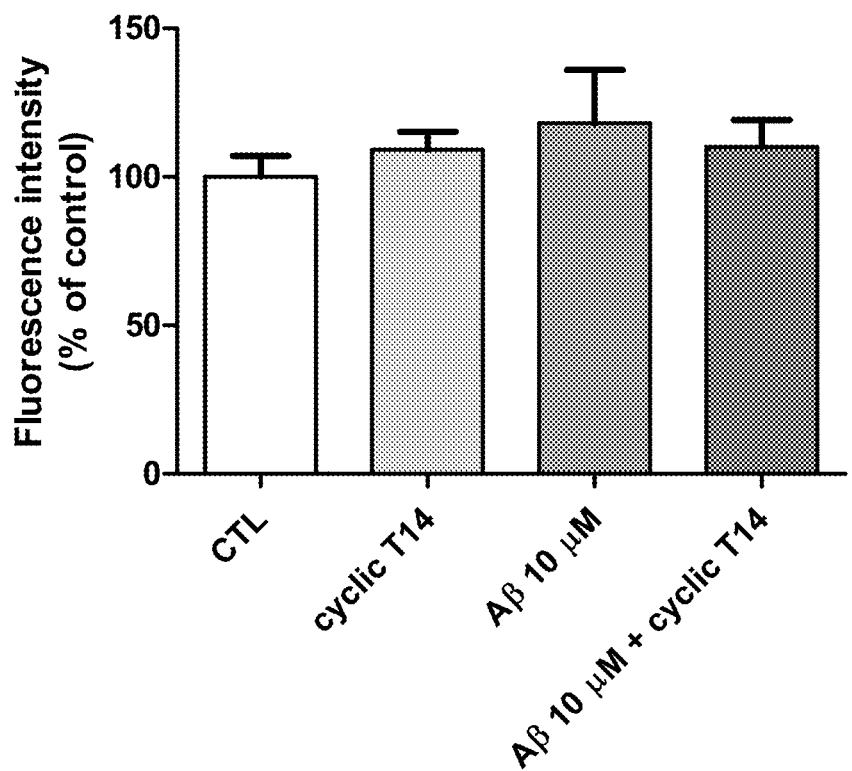
FIG. 10 is a bar graph showing the intracellular levels of $Ca^{2+}$ in rat brain slices after 2 hours of different treatments. Data represents mean±SEM, N=4.

As shown in FIG. 10, although not wishing to be bound by this theory, the inventor believes that β-amyloid (Aβ) is capable of either (i) simultaneously binding to both the orthosteric and the allosteric binding sites of the α7 nicotinic-receptor, or (ii) non-specifically binding to one either of these sites. The inventor has found that cyclical T14 acts as an antagonist at the allosteric site.

Drug Design

The inventor believes that it will be possible to use the particular conformation of Cyclic T14 to design a much smaller chemical compound which nonetheless still mimics the three-dimensional form of Cyclic T14 and is able to cross the blood-brain barrier more readily.

Example 13—Physico-Chemical Characterisation of Cyclic T-14 (i.e. Referred to as "NBP14")

Background

The solubility of a compound in aqueous and organic solutions strongly affects its ability to cross physiological barriers in the body, such as gastric or enteral. In the case of drugs targeting brain diseases, e.g. dementia, an additional barrier has to be crossed, the Blood-Brain Barrier. The partition coefficient, also known as Log P, evaluates the ability of a compound to solubilize in water and organic solvent, which correlates with the capacity of a compound to cross the different biological barriers.

Detailed Methods
Solvent Preparation

Saturation of the solvents was performed as follows. 1-octanol was agitated in the presence of water for 24 h at room temperature. mQ water was agitated in presence of 1-octanol for 24 h at room temperature. Then the solutions were left to equilibrate overnight at room temperature. Saturated solvents were collected, using syringes and needles, and stored at room temperature until further use.

Shake-Tube Method

Saturated water and saturated i-octanol were placed in a glass tube in the following ratios: Each tube contained the equivalent of 0.25 mg of cyclic T14. All tubes were then mixed for 4 h at room temperature. After agitation the tubes were left at room temperature to equilibrate.

Standard Curve

The concentrations of cyclic T14 used for the standard curve were: 0.5 mg·ml$^{-1}$, 0.25 mg·ml$^{-1}$, 0.13 mg·ml$^{-1}$, 0.066 mg·ml$^{-1}$, 0.033 mg·ml$^{-1}$ and 0.016 mg/ml$^{-1}$. The absorbance of the standard curve was measured at 280 nm.

Sample Analysis

Both fractions of each sample were collected separately using a syringe with needle. The absorbance of all fractions was measured at 280 nm and the concentration of all the fraction was estimated based on the standard curve. The partition coefficient of cyclic T14 was calculated using the following equation:

Log $P$=Log (Concentration in Octanol/Concentration in Water)

The results from each condition were averaged in order to obtain the Log P of cyclic T14.

Results and their Implications

The average Log P of cyclic T14 is −0.5899. A negative value for Log P means that the compound is more likely to be hydrophilic. However, a Log P close to 0 corresponds to a compound with the ability to be soluble in a lipophilic environment as well. Hence, NBP14 can be formulated to cross the BBB.

Example 14—Effects of Tao and Cyclic T-14 (i.e. NBP-14) in PC12 Cells

To characterize further the protective effects of NBP-14 against T30 toxicity, the inventors have determined the concentration-effect on three in vitro systems ((A) Calcium influx; (B) AChE release; (C) Cell viability), as detailed in the Methods section below.

Methods (A) Calcium Influx

PC12 cells are plated in 200 µl of complete growth medium the day before the experiment in 96 well plates. On the day of the experiment, the Fluo-8 solution (Abcam) is prepared (as provider protocol). Subsequently, 100 µl of growth medium is removed and 100 µl of Fluo-8 solution is added. Treatments with T30 and NBP-14 are added and incubated for 30 minutes in the incubator and 30 minutes room temperature.

After 1 hour, the plate is placed in the fluorescence plate reader (Fluostar). Before reading the fluorescence, acetylcholine (ACh) 100 µM is prepared and placed in the Fluostar injector. For each well, the reading will be formed by a basal fluorescence followed by acetylcholine injection that will induce an increase of calcium via nicotinic receptors. The effects of T30 and NBP-14 are then evaluated.

(B) AChE Release

The protocol used to detect changes in AChE activity is the same as described previously.

(C) Cell Viability

A Cell Counting Kit-8 (CCK-8) was used as an improvement of the SRB technique used before. By utilizing the highly water-soluble tetrazolium salt WST-8, CCK-8 produces a water-soluble formazan dye upon reduction in the presence of an electron carrier. WST-8 is reduced by dehydrogenases in cells to give a yellow colored product (formazan), which is soluble in the tissue culture medium. The amount of the formazan dye generated by the activity of dehydrogenases in cells is directly proportional to the number of living cells. PC12 cells are plated in 200 µl of complete growth medium the day before the experiment in 96 well plates. Treatments with T30 and NBP-14 are added and incubated for 1 hour in the incubator.

Subsequently, 100 µl of growth medium is removed and 10 µl of CCK-8 (Cell Counting Kit-8) solution is added. The plate is incubated for 2 hours in the incubator and then placed in the absorbance plate reader. The absorbance must be measured at 450 nm.

(A) Calcium Influx

As stated previously, T30 is a positive allosteric modulator of the α7 nicotinic receptor. Hence the primary agonist acetylcholine was used to benchmark the control calcium influx as 100%). T30 (5 uM) enhanced this effect until 171.05%±6.21%; N=3. Increasing concentrations of NBP-14 (5, 7, 9, 10, 20, 50, 70, 1000, 5000 nM) were subsequently added to determine the antagonism of these T30-induced increases. The values are (respectively) (%): 134.2497±6.85, 120.8612±8.65, 113.9162±8.82, 140.776±12.16, 115.83±7.67, 110.3213±13.21, 125.9596±0.1, 99.85±0.32, 115.1942±9.84, 79.99±14.04. FIG. 13 shows that NBP-14 blocks T30 effects in a concentration manner, being protective at low nanomolar range.

(B) AChE Release

Figure 14:
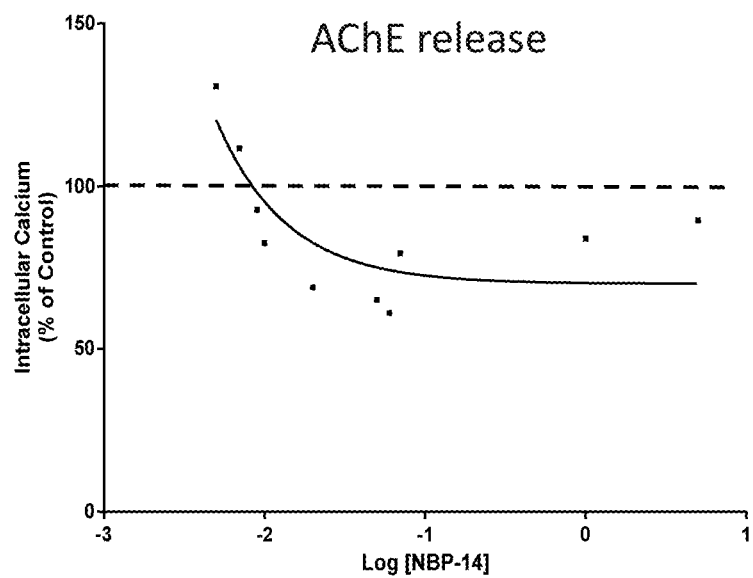
FIG. 14 is a graph showing the protective effect of different concentrations of NBP-14 (5, 7, 9, 10, 20, 50, 70, 1000, 5000 nM) on AChE release induced by T30. The values were fitted to a non-linear curve with the logarithm of the inhibitor concentrations, NBP-14, versus the response of the T30, by using GraphPad Prism.

As described above, PC12 cells respond to the toxic effect of T30 with a 'compensatory' response, i.e. an increase in released AChE activity: 169.45%±2.11%; N=3. The inventors determined the dose-dependent effect of NBP-14 against 5 uM T30. The results show (FIG. 14) that NBP-14 protects from AChE compensatory effects at high nanomolar concentrations. The values are (respectively) (%): 130.73±1.84, 111.68±2.26, 92.78±0.99, 82.56±2.38, 68.90±0.92, 65.12±1.32, 61.04±0.97, 79.43±1.69±1.24, 83.91±1.24, 89.55±1.25.

(C) Cell Viability

Figure 15:
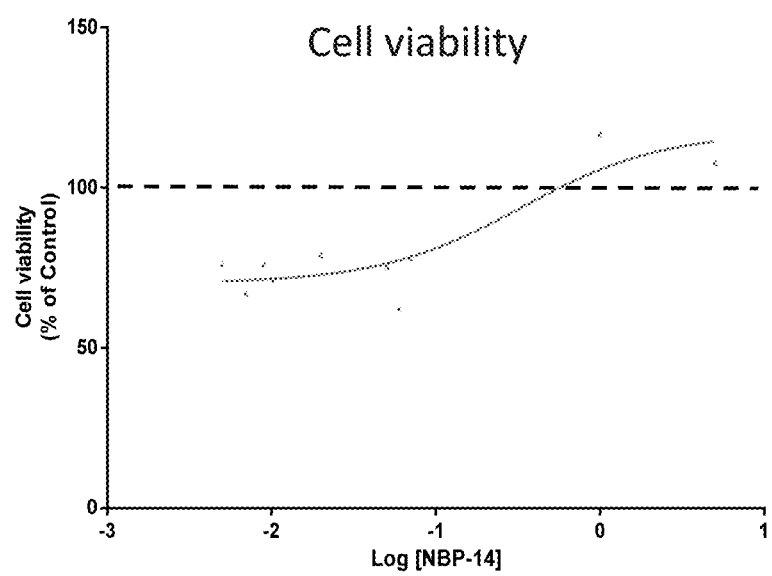
FIG. 15 is a graph showing the protective effect of different concentrations of NBP-14 (5, 7, 9, 10, 20, 50, 70, 1000, 5000 nM) on cell viability induced by T30. The values were fitted to a non linear curve with the logarithm of the inhibitor concentrations, NBP-14, versus the response of the T30, by using GraphPad Prism.

T30 (5 uM) induces a 25% (74.309%±2.87%; N=3) decrease of cell viability that is progressively blocked by NBP-14 in a concentration-effect manner (FIG. 15). The values are (respectively) (%): 76.25±7.51, 67.04±4.35, 76.04±4.22, 71.36±1.64, 79.02±10.22, 75.19±3.9, 62.43±3.01, 78.10±2.16, 116.65±3.62, 107.79±5.10. NBP-14 protects from T30 induced cell death in the high nanomolar range.

Example 15—Effects of T30 and Cyclic T-14 (i.e. NBP14) on In Vitro Cortical Networks in Rat Brain Slices Background The T30 peptide is a 30-amino acid segment of acetylcholinesterase (AChE), from which the T14 is also cleaved. Both induce the same effect suggesting their active sequence is present on the T14, and in turn present on the T30. The research has already shown the bioactivity of T14 on mammalian brain slices as a highly modulatory agent. The effects of the T14 have been reported to modulate cortical networks, inducing both excitation and inhibition at different concentrations: at low concentrations the peptide triggers enhanced calcium influx via the alpha-7 receptor, but high concentrations induce such excessive amounts of calcium that the channel inactivates (Badin et al., 2013; Bon and Greenfield, 2003), as well as triggering neuronal plasticity (Greenfield et al., 2004).

In order to gain further understanding of the actions of T14/30 on whole cortical networks, the relatively recent technique of voltage-sensitive dye imaging (VSDI) was used in order to monitor the dynamics of collective neuronal population activity, 'neuronal assemblies', in brain slices on a temporal scale of milliseconds (ms, commensurate with physiological events) and micrometres (µm). Such a technique exploits the sensitivity of specific lipophilic molecules containing a fluorescent core to changes in electrical potentials (Tominaga et al., 2000). Due to their lipophilic nature, these dye molecules embed themselves in cell membranes, and alter their fluorescence reading with regards to the voltage potential across that specific membrane, which are captured with a millisecond-resolution high-speed camera. As a result, imaging using voltage-sensitive dyes provides a direct and on-line readout of electrical potential changes across neuronal cell membranes with an unparalleled spatiotemporal resolution.

Using this technique the inventors can obtain comprehensive sets of data on neuronal population activity such as (a) the intensity of the response in any given area, from which (b) the spread of elicited neuronal assemblies can be measured, and from this parameter (c) the velocity of propagation of the activity wave-front from the point of initiation (d) measured as the slope of the spread. Each of these parameters have been measured independently for two experiments carried out so far: i) an investigation of the effects induced by increasing concentrations (0.5, 0.75, 1 & 5 µM) of T30 on cortical population activity and responsiveness, and 2) assessing the antagonistic effects of NBP-14 on a single, relatively high (1 uM), T30 concentration.

Technique used: voltage-sensitive dye imaging (Di-4-ANEPPS) of thalamocortical (TC) p14 rat (Wistar) brain slices.

Stimulation paradigm: 40 Hz (consistent with thalamo-cortical recurrent stimulation) paired pulse stimulation.

Perfusion paradigm: epochs carried out in two phases—for every drug perfusion (say: control, 0.1 uM T30 etc.), the new perfusion was applied and left to perfuse for 15 minutes before starting the recording period (15 minutes also), such that the drug had time to reach its actual concentration and induce its concentration-dependent effects once recording. Meaning one perfusion epoch lasted 30 minutes, with the recording only taking in account the last 15 minutes of its respective perfusion epoch.

Detailed Methods

Brain Slice Preparation

Male Wistar rats (14-17 day old; 15 individual animals in total) were anaesthetised using isoflurane: 10 mL 100% w/w isoflurane was applied to the cotton bed at the bottom of an anaesthesia chamber (glass box 20×15×15 cm) where rats were then placed for ~45 seconds until onset of anaesthesia. The hind paw of each anaesthetised rat was pinched to check for appropriate depth of anaesthesia. Once anaesthesia was confirmed, rats were quickly decapitated before immersing the brain in oxygenated ice-cold artificial cerebrospinal fluid ('slicing' aCSF in mmol: 120 NaCl, 5 KCl, 20 $NaHCO_3$, 2.4 $CaCl_2$), 2 $MgSO_4$, 1.2 $KH2PO_4$, 10 glucose, 6.7 HEPES salt and 3.3 HEPES acid; pH: 7.1) for 7-8 minutes, the time taken to cut the brain into slices. Para-saggital sections (400 μm thick) were cut from a block of brain containing both Thalamus (VPN) and primary somato-sensory cortex (barrel field) using a Vibratome (Leica VT1000S) and transferred to a bubbler pot containing aCSF at room temperature ('recording' aCSF in mmol: 124 NaCl, 3.7 KCl, 26 $NaHCO_3$, 2 $CaCl_2$, 1.3 $MgSO_4$, 1.3 $KH_2PO_4$ and 10 glucose; pH: 70.1), which was identical to that which was used during electrophysiological recordings and VSDI. Slices were left in oxygenated (95% $O_2$-5% $CO_2$) 'recording' aCSF to recuperate for at least 1 hour before VSD staining.

VSD Setup

Slices were placed in a dark, high humidity chamber filled with aCSF bubbling with 95% $O_2$-5% $CO_2$. The dye solution (4% 0.2 mM styryl dye pyridinium 4-[2-[6-(dibutylamino)-2-naphthalenyl]-ethenyl]-1-(3-sulfopropyl)hydroxide (Di-4-ANEPPS, Invitrogen, Paisley, UK) (Tominaga et al., 2000) in aCSF 46%, fetal bovine serum 46%, DMSO 3.5% and cremophore EL 0.4%) was then applied to the slices as previously described (Badin et al., 2013). When starting VSD recordings, slices were placed in the recording bath on a small piece of filter paper to keep slice alive and was weighed down appropriately using a home-made plastic grid placed atop the slice. Because of the fluorescent VSD, all of the handling of slices during and after staining with Di-4-ANEPPS was carried out in almost complete darkness in order to keep the detrimental effects of photo-toxicity and bleaching to a minimum. VPN (where stimulating electrodes were placed) was identified with respect to distance from the tip of the hippocampus and to the side of the internal capsule.

Stimulating electrodes, with impedance (measured at 1000 Hz): 500 kΩ, were placed in VPN, where paired-pulse stimulations (2×100 μs in duration; 25 milliseconds inter-stimulus interval—ISI—paired-pulse at 40 Hz) were triggered to evoke fast-paced propagating waves of activity in the innervated barrels using Spike 2 V6.0 (CED Ltd, Cambridge, UK) with respect to appropriate ISI. Such transient 'neuronal assemblies' were recorded by acquiring 16-bit images with a 1 ms resolution using MiCAM Ultima ultra-fast imaging system coupled to a digital camera (Brain Vision MiCAM Ultima R3-V20 Master) with Ultima 2004/08 imaging software (Brain Vision). Light was generated using an Osram halogen xenophot 64634 HLX EFR Display/Optic lamp and was filtered to emit green light (530±10 nm) using a MHF-G150LR (Moritex Corporation). The emitted fluorescence was passed through a dichroic mirror and a >590 nm high-pass filter as described previously (Collins et al., 2007; Devonshire et al., 2010a; Devonshire et al., 2110b; Grandy et al., 2012; Mann et al., 2005).

Drug Preparation & Application

T30 and NBP-14 solutions were prepared fresh at the start of each experiment, stock solution aliquots were added to 'recording' aCSF as appropriate and bath applied at a constant rate of 1.5 mL per min perfusion using a Minipulse 3 pump (Gilson Scientific Ltd, Bedfordshire, UK). Perfusion conditions were split in 2: the first part consisted of a 15 minute perfusion with no recording taking place, such that the appropriate concentration could be achieved in the recording bath before starting the second part of the perfusion condition—where the recording took place for the next 15 minutes of perfusion (30 averaged snapshots)—giving a total of 30 minutes per perfusion condition.

Data Analysis and Statistics

VSDI produced 4×4 mm (100×100 pixels) 2-Dimensional images from which critical data were extracted such as the time-course of activation, spread and intensity of the overall elicited signal. For each VSDI experiment, each snapshot's data between 0 and 200 ms after stimulation, encapsulating the peak response, had their parameters measured and averaged for each condition (total of 30 snapshots per condition for both T30 and T30 v NBP-14 experiments). In order to achieve this, a region of interest (ROI) was selected over the active area, which encompassed the width of the maximum response after it had been filtered with a threshold that isolated active pixels as those showing activity greater than 20% of the maximum activity recorded within that region of interest. Such data were then compiled to produce detailed quantitative graphs of the extent of activation intensity (FIGS. 16A-16B, 17, 18) as well as qualitative 'space-time' maps (FIG. 19) to measure the effects recorded as well as to produce accurate visual representations of the spatio-temporal data acquired. All statistical tests (Analysis of Variance—ANOVA) were performed using non-linear mixed effects models fitted to the data using R Studio while all the data handling and analysis was performed using Mathematica 8 (Wolfram Research, USA). For all statistical tests $P<0.05$ was considered significant. Data are expressed as mean±S.E.M.

Results and Discussion

Figure 16A:
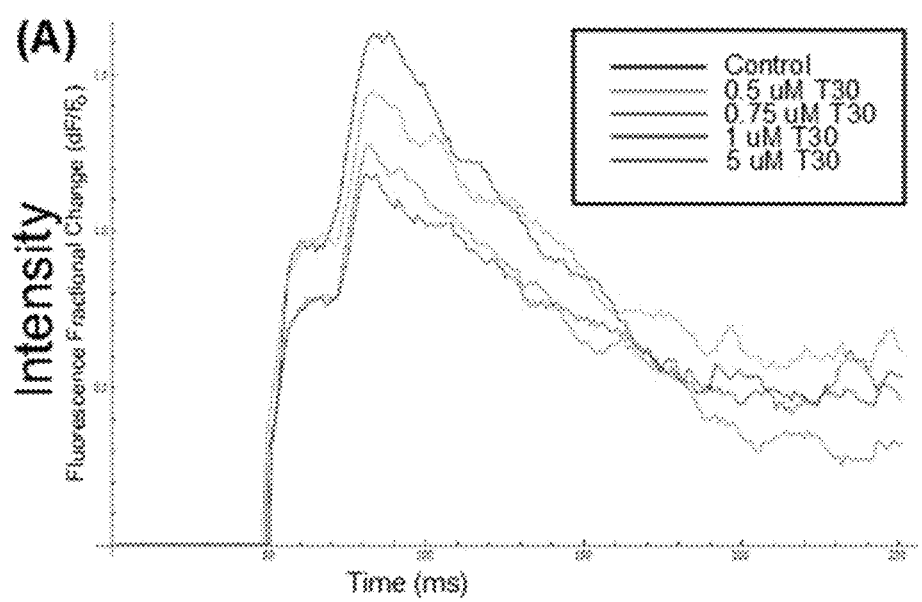
FIGS. 16A and 16B include graphs showing overall cortical response to thalamic electrical stimulation under different T30 concentrations. (A) Synchrony of neuronal population activity, measured as fractional change in fluorescence intensity. (B) Spread of population activity, measured as the number of active pixels—defined as pixels showing more than 20% of the max intensity given off by any single pixel within the Region of Interest.
Figure 16B:
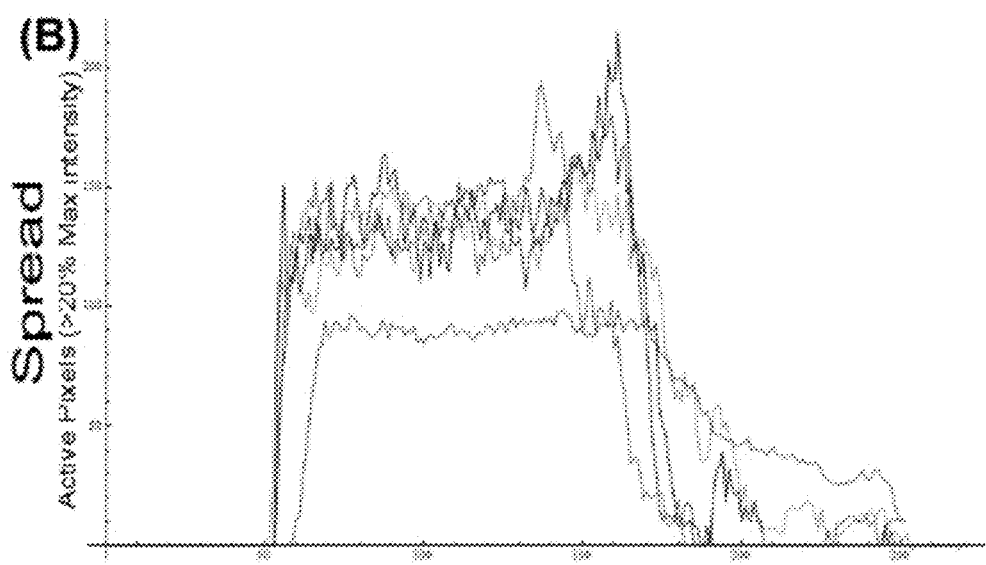

FIGS. 16A-16B show the effect of increasing dose of T30 on (A) intensity of emitted fluorescence, as well as (B) spread of active pixels. Each pixel has dimensions 40×40 μm meaning its specific fluorescence arises from the activity of less than 10 independent neurons. As the T30 concentration increases within the recording bath, the intensity of fluorescence given off by active pixels diminishes. This indicates a de-synchronisation of triggered neuronal population activity, as sizeable and simultaneous neuronal membrane depolarisation from a single pixel amounts to a higher fluorescence reading, the opposite effect is seen here (less synchrony). Additionally, here a 40 Hz paired-pulse stimulation paradigm is used, as can be seen from the Intensity graph (FIG. 16A). The results show that not only is the overall fluorescence reduced as a result of T30 treatment, but that the second pulse (which is triggered at 75 ms, 25 ms after the first one—40 Hz paired pulse) shows a much reduced facilitation compared to the magnitude of the original pulse.

Furthermore, as can be seen from the spread graph (FIG. 16B), the spread of cortical assemblies is not significantly affected by T30 treatment until very high levels (5 uM) are achieved, this corroborates the theory that T30 acts as a modulating agent on whole cortical networks. It is also important to keep in mind that the different parameters highlighted by VSDI, such as the velocity of propagation, the spread and the intensity of fluorescence, often rely on underlying principles of cortical dynamics which are not necessarily related, meaning each of these parameters must be analysed separately and that their results must at first be interpreted independently from each other.

Figure 17:
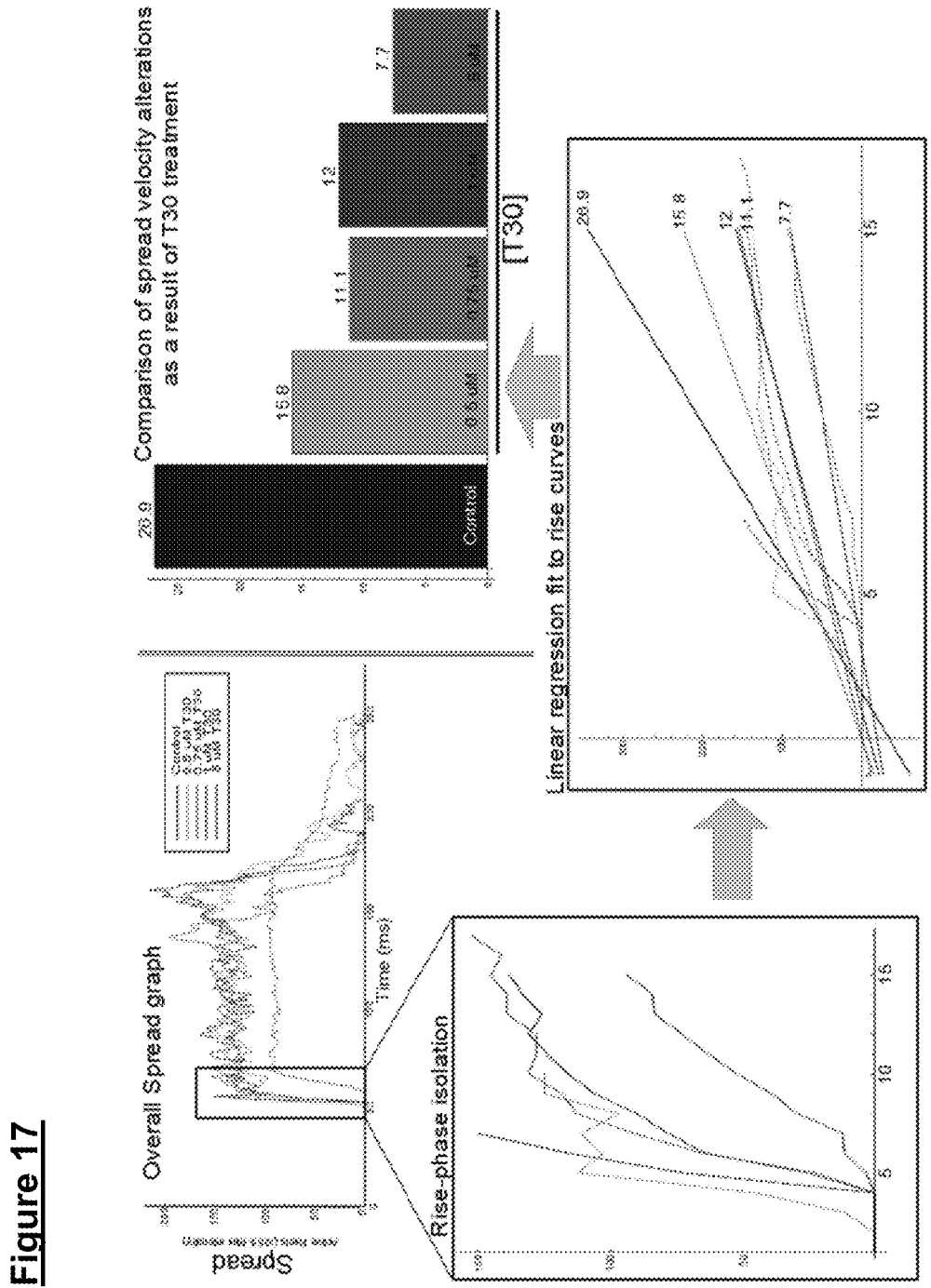
FIG. 17 shows isolation and linear analysis of the rise phase of the spread of assemblies under different T30 concentrations, as seen from FIGS. 16A and 16B. Increasing concentrations of T30 show a dose-dependent decrease in the linear slope, equivalent to the velocity of propagation of the assembly.

FIG. 17 shows the effect of increasing T30 application upon the dynamics of assembly initiation and propagation were investigated in greater detail. FIG. 17 shows that T30 induces a reduction in neuronal activity propagation speed (here acquired as the slope of the rise phase), consistent with a decrease in the synchrony of cortical networks, as shown in FIGS. 16A-16B, with a maximum of a 3.5-fold decrease in propagation speed under 5 µM T30 treatment. Resulting from the above, and previous experiments, it was concluded that the 5 µM T30 concentration was too high as it was probably inducing sufficient calcium influx to be at the threshold for inactivation of the ion channel, thus leading to a mixture of excitatory/inhibitory effects depending on the sensitivity of the particular preparation, as reported previously (Bon and Greenfield, 2003). The inventors therefore used a lower, yet sufficiently potent, concentration, 1 µM T30, to carry out the subsequent experiments exploring the possible antagonistic effects of NBP14. This T30 concentration, although still quite high, was chosen because of the nature of the present study, where an inevitable dilution effect is to be expected as the peptide penetrates the brain slice. Meanwhile, for NPB14, they used increasing concentrations of: 0.1, 5, 100 & 300 nM, i.e. 2 to 4 orders of magnitude lower than the concentrations of T30, since previous in vitro studies in PC 12 cells had indicated a far higher affinity for alpha-7 nicotinic acetylcholine receptors compared to that of T30.

Figure 18:
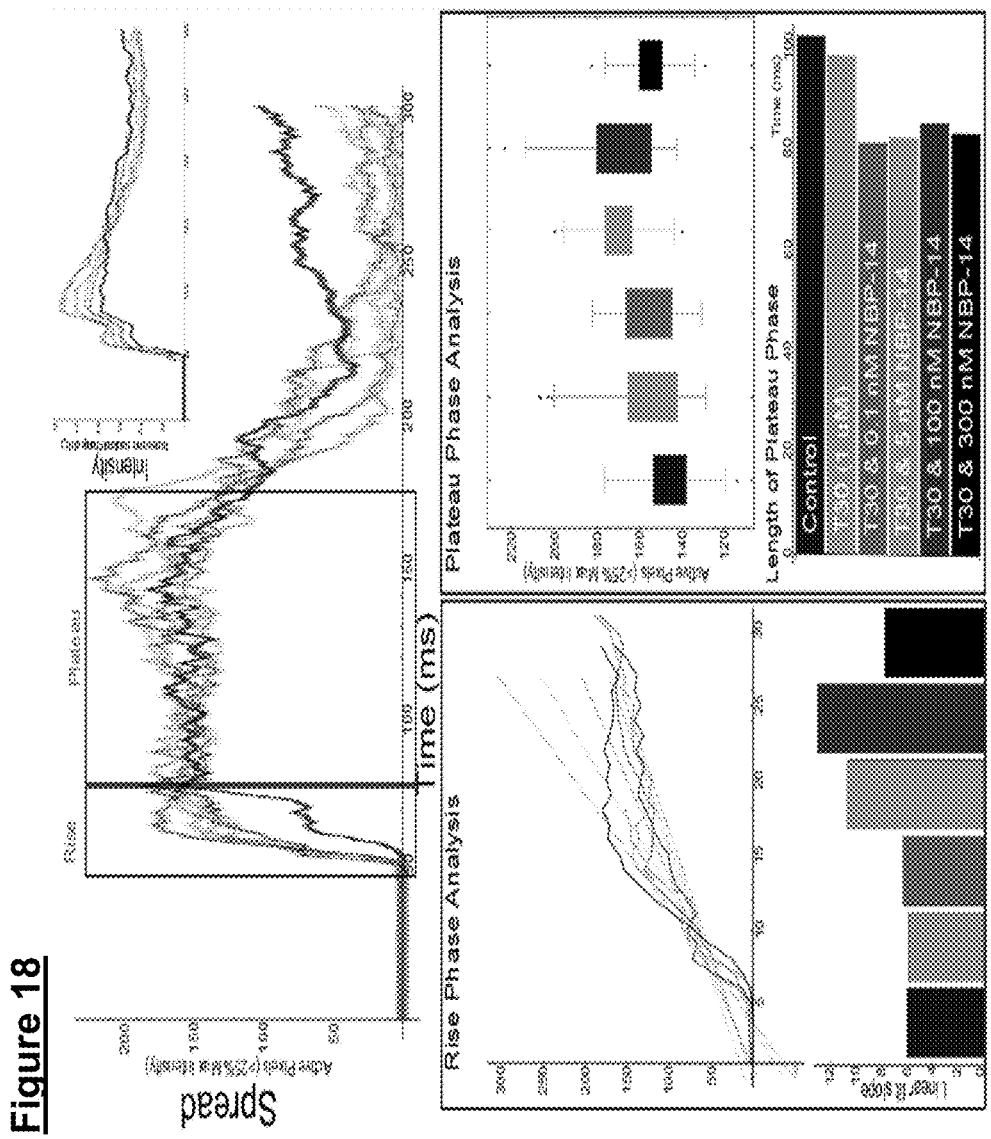
FIG. 18 shows analysis of spread dynamics of thalamo-cortically-evoked neuronal assemblies under T30 and NBP-14 treatment, n=3. Analysis of the rise phase (left panel) shows a latent effect of T30 in increasing the slope (velocity) of propagation. The slope shows significant increases only about 45-60 minutes after initial T30 perfusion (yellow bar, effects become apparent during orange perfusion—with perfusion of 5 nM NBP-14). This sharp increase trend is slowed down during the 100 nM NBP-14 perfusion (red bar), and then reversed back to baseline levels during the final 300 nM NBP-14 perfusion (black bar). Plateau phase analysis (right panel) shows a similar profile of effects. The top panel shows a box and whisker plot averaging the behaviour of the assemblies' spread under the different drug treatments: a similar trend as in the rise-phase slope analysis can be seen, and though non-significant, the trend remains that $T_{30}$ gradually increases the spread of evoked assemblies until a sufficiently high NBP-14 concentration reaches the recording bath (100 nM) where this excitatory trend is reversed back towards control levels (blue) at 300 nM NBP-14 perfusion (black)

FIG. 18 shows antagonism of T30 effects by increasing concentrations of NBP-14. The Figure shows the antagonistic nature of NBP-14 on the modulatory effects induced by T30 perfusion on neuronal populations. An important consideration is the dilution factor as T30 penetrates slices, including all physiological processes potentially still present and active within brain slices, such as proteases, neurotransmitter uptake and the density of the extracellular matrix; it therefore seems highly probable that a concentration of 1 µM T30 would take time to induce its full effects (45-60 minutes, as suggested by the data presented above). Bearing this in mind, the effects of T30 become apparent during the 5 nM NBP-14 perfusion (orange line/bar), after which the trend induced by T30 is reversed back towards baseline (blue bar/line).

It is important to also note that NBP-14 has been shown to be inert, never inducing any modulatory effects on its own, implying that the effects seen here are at first attributable to T30, and their reversal to antagonism by increasing concentrations of NBP-14. Importantly, the vast majority of T14 effects are reduced back to control levels under the 300 nM NBP-14 perfusion, while T30 is perfused at a concentration of 1000 nM. This suggests a significantly higher affinity of NBP-14 for its target compared to T30.

Figure 19:
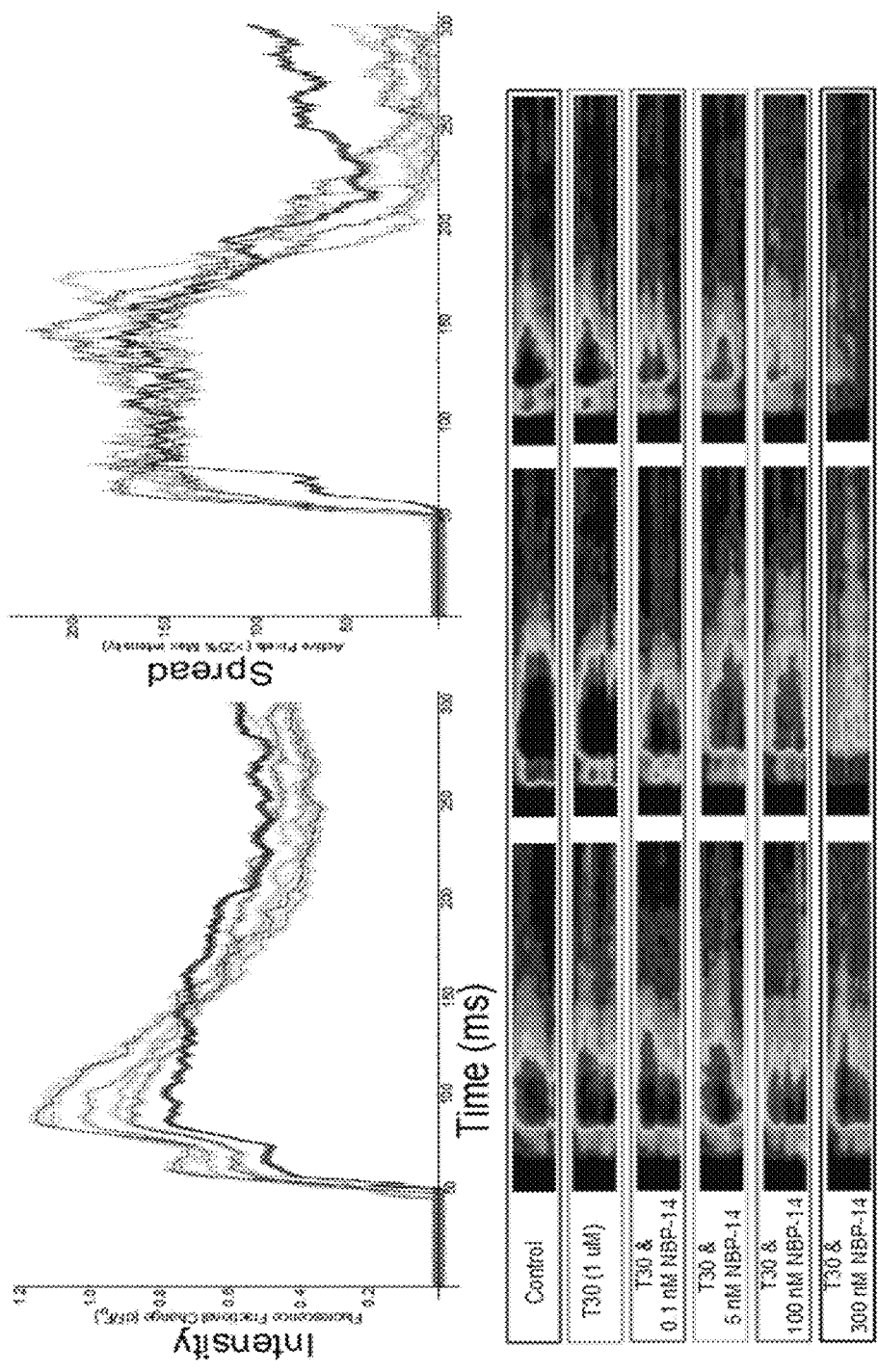
FIG. 19 shows qualitative results from the three experiments (ie left, centre and right-hand columns) where $T_{30}$ effects were tested against increasing concentrations of NBP-14 (0.1, 5, 100 & 300 nM). Top panel shows the two main averaged-data graphs: left—Intensity of fluorescence signal, and right—spread of evoked assemblies. Bottom panel shows 'space-time' maps mapping the activity of a row of pixels lying over the area of interest (y-axis) over time (310 ms total, x-axis) for each perfusion conditions. The drastic reduction in fluorescence intensity as a result of T30 and NBP-14 co-perfusion is clearly evident, as it is on the Intensity graph. Note: the space-time maps are labelled with their respective perfusion (left), and are colour-coded to their corresponding traces both in the intensity (right) and spread (left) graphs.

FIG. 19 shows qualitative results from the three experiments (ie left, centre and right-hand columns) where T30 (1 µM) effects were tested against increasing concentrations of NBP-14 (0.1, 5, 100 & 300 nM). Top panel shows the two main averaged-data graphs: left—Intensity of fluorescence signal, and right—spread of evoked assemblies. Bottom panel shows 'space-time' maps mapping the activity of a row of pixels lying over the area of interest (y-axis) over time (310 ms total, x-axis) for each perfusion conditions. The drastic reduction in fluorescence intensity as a result of T30 and NBP-14 co-perfusion is clearly evident, as it is on the Intensity graph. Note: the space-time maps are labelled with their respective perfusion (left), and are colour-coded to their corresponding traces both in the intensity (right) and spread (left) graphs.

REFERENCES

Badin, A. S., J. Eraifej, and S. Greenfield. 2013. High-resolution spatio-temporal bioactivity of a novel peptide revealed by optical imaging in rat orbitofrontal cortex in vitro: Possible implications for neurodegenerative diseases. *Neuropharmacology.* 73C:10-18.

Bon, C. L., and S. A. Greenfield. 2003. Bioactivity of a peptide derived from acetylcholinesterase: electrophysiological characterization in guinea-pig hippocampus. *Eur J Neurosci.* 17:1991-1995.

Collins, T. F., E. O. Mann, M. R. Hill, E. J. Dommett, and S. A. Greenfield. 2007. Dynamics of neuronal assemblies are modulated by anaesthetics but not analgesics. *Eur J Anaesthesiol.* 24:609-614.

Devonshire, I. M., E. J. Dommett, T. H. Grandy, A. C. Halliday, and S. A. Greenfield. 2010a. Environmental enrichment differentially modifies specific components of sensory-evoked activity in rat barrel cortex as revealed by simultaneous electrophysiological recordings and optical imaging in vivo. Neuroscience. 170:662-669.

Devonshire, I. M., T. H. Grandy, E. J. Dommett, and S. A. Greenfield. 2010b. Effects of urethane anaesthesia on sensory processing in the rat barrel cortex revealed by combined optical imaging and electrophysiology. *Eur J Neurosci.* 32:786-797.

Grandy, T. H., S. A. Greenfield, and I. M. Devonshire. 2012. An evaluation of in vivo voltage-sensitive dyes: pharmacological side effects and signal-to-noise ratios after effective removal of brain-pulsation artifacts. *Journal of neurophysiology.* 108:2931-2945.

Greenfield, S. A., T. Day, E. O. Mann, and I. Bermudez. 2004. A novel peptide modulates alpha7 nicotinic receptor responses: implications for a possible trophic-toxic mechanism within the brain. *J Neurochem.* 90:325-331.

Mann, E. O., T. Tominaga, M. Ichikawa, and S. A. Greenfield. 2005. Cholinergic modulation of the spatiotemporal pattern of hippocampal activity in vitro. *Neuropharmacology.* 48:118-133.

Tominaga, T., Y. Tominaga, H. Yamada, G. Matsumoto, and M. Ichikawa. 2000. Quantification of optical signals with electrophysiological signals in neural activities of Di-4-ANEPPS stained rat hippocampal slices. *Journal of neuroscience methods.* 102:11-23.

Example 16—Effects of NBP 14 in the Freely Moving Rat

Background

Unlike animal models for Alzheimer's disease, the rat model for hemi-Parkinsonism is very well established and readily quantifiable. Accordingly, a unilateral intra striatum injection of the T30 was administered to observe any behavioural effects of the toxin. In a subsequent experiment, the potential protective effects of NBP14 were observed against the well-known neurotoxin 6-hydroxydopamine (6-OHDA), which led to DA neuron loss on the injected side whilst sparing the contralateral DA neurons. NBP-14 was administered via implanted cannula into the medial forebrain bundle (MFB). 6-hydroxydopamine was injected at 10 mg/kg.

Detailed Methods

Animals are anaesthetized using Ketamine (10%; 0.1 ml/kg body weight) and Xylazine (2%; 0.01 ml/kg). The animals are then stereotactically injected into the MFB with 2 μL 6-OHDA at a concentration of 20 mg/ml in 0.02% ascorbic acid. Lesion coordinates are set according to bregma and dura in cm: L-1.7 mm; AP-3.6 mm; DV-8.0 mm. Following the injection (injection rate 2 μl/5 min), the injecting needle is left for another 1 minute to avoid back flow and then slowly retracted.

Paw Placement Test (Cylinder Test): This test assesses a rat's independent forelimb use to support the body against the walls of a cylindrical enclosure. The test takes advantage of the animals' innate drive to explore a novel environment by standing on the hindlimbs and leaning towards the enclosing walls. To perform this test, rats are placed individually in a glass cylinder (21 cm diameter, 34 cm height) and wall exploration is recorded for 3 minutes. No habituation to the cylinder prior to recording is allowed. Wall exploration is expressed in terms of the ratio between the intact (R) and impaired legs (L) and calculated as the values of intact right+both forelimbs divided into the values of impaired left+both forelimbs (R/L). The paw placement test is conducted on Day −1 to obtain baseline data, on Day 1 for selection and on days 2.

Selection criteria (Day1): According to Paw placement test all animals with statistically significant difference between paws will be included in the study (ratio between the intact (R) and impaired legs (L) is expressed as the values of intact right+both forelimbs divided into the values of impaired left+both forelimbs).

The results from all tests will be presented as MEAN group value±SEM. Analysis of the data by one-way ANOVA following by Tukey test will be applied to determine significance of treatment effects. This study was performed following approval of an application form submitted to the Committee for Ethical Conduct in the Care and Use of Laboratory Animals that states that the present study complied with the rules and regulations set forth.

Figure 20:
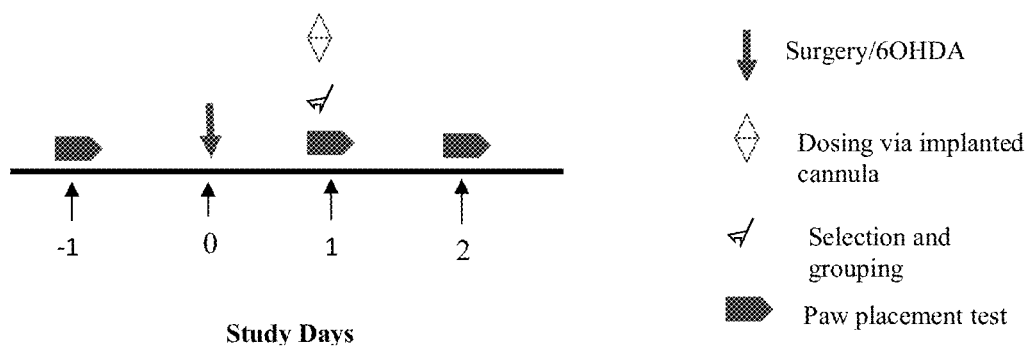
FIG. 20 shows a schematic of the procedure followed during the in vivo testing of NBP-14. The day before the surgery all animals are tested in order to reveal any impairment. The day of the surgery is considered as day 0 of the study. On day one a paw placement test allowed the selection of the 16 out of 24 best subjects in order to inject with the vehicle or NPB-14. On day 2 a paw placement test was performed.

FIG. 20 summarises the procedure followed during the in vivo testing of NBP-14.

Results

Effects NBP14

Figure 21:
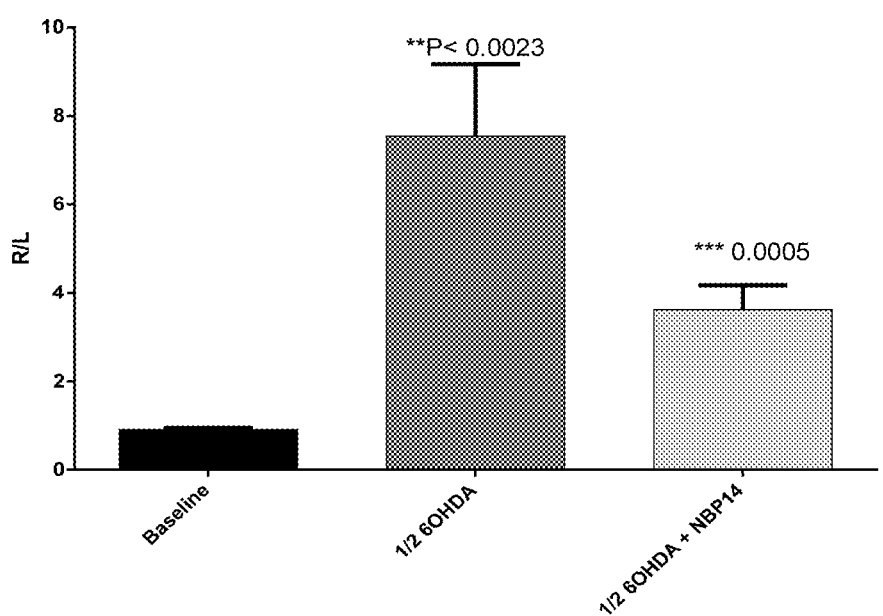
FIG. 21 shows the effect of NBP-14 against 6-OHDA in comparison with Baseline and 6OHDA alone in the Paw placement test. 6-OHDA P<0.01 and 6OHDA+NBP14 *P<0.001 vs Baseline. (N=8)

Analysis of the paw placement R/L ratio reflects unilateral injury of motor function. On day 2, i.e. two days post 6-OHDA injection and one day after injection of NBP-14, there was a significant difference in the R/L ratio of paw placement between 6-OHDA vehicle and treated: 7.54±1.63 vs. 3.62±0.55, respectively ($p<0.05$). Treatment with NBP-14 improved mobility of impaired forelimb after one dosing as was shown in the paw placement test (FIG. 21).

Example 17—Effects of T30 and NBP14 on APP and Amyloid

Background

It is has already been established that an excess of calcium can trigger abnormal cleavage of Amyloid Precursor Protein (APP) and hence Amyloid beta (A13) release (Hartigan & Johnson, 1999; Cai et al., 2012). Since the inventors have shown that T30 increases calcium influx by about 70% in PC12 cells, it is possible that such a calcium increase will trigger the production of amyloid and a consequent decrease in the full length APP molecule.

Detailed Methodology: Detection of APP

Protocol for Solubilizing Protein

PC12 cells are plated with growth medium in Petri Dishes for a week in order to have enough protein to detect APP in PC12 membranes and treated for 1 hour with T30 and NBP-14 before solubilizing the protein. Once the cells have grown until 90% confluence, the growth medium is removed and cells are re-suspended in 2 ml of HBSS. The cells suspension is transferred to a 15 ml tube and centrifuge 5 minutes at 1000 rpm. Then the supernatant is discarded and the pellet is re-suspended in Lysis buffer (20 mM Tris, 137 mM NaCl, 1% Triton X-100, 2 mM EDTA; pH 8) plus protease inhibitors (1 μl:1 ml PMSF and 3 μl:1 ml Aprotinin) and triturated by using a Polytron for 10 seconds. Subsequently, the triturated pellet is distributed in 1.5 ml eppendorfs and rotated or shaken for 2 h at 4° C. After 2 h, the eppendorfs are centrifuged at 15000 rpm for 20 minutes and the supernatant is kept. The Bradford reagent is used to quantify the protein contained in each eppendorf.

Protocol for Electrophoresis

For APP detection, an aliquot of 25 μg of protein is used. Before starting the protocol the reagents are prepared as follows:

Lower Gel (10%) (20 Min to Polymerize)

For 10 ml (2 gels):3.6 ml H2O MQ, 2.42 ml Acrilamide and 1.3 ml Bis-Acrilamide, 2.5 ml Tris-HCl 1.5 M pH 8.8, 0.11 ml SDS 10%, 0.06 ml Ammonium persulfate 10%, 6.67 μl TEMED (last ingredient).

Upper Gel (5%) (20 Min to Polymerize)

For 5 ml (2 gels): 3.67 ml H2O MQ, 0.48 ml Acrilamide and 0.26 ml Bis-Acrilamide, 0.625 ml Tris-hCl 1 M pH 6.8, 0.05 ml SDS 10%, 25 μl Amonium persulfate 10%, 5 μl TEMED.

Tris-HCl 1.5 M pH 8.8

For 100 ml: 18.16 gr Tris Base, qsp 100 ml H2O MQ, pH 8.8.

Tris-HCl 1 M pH 6.8

For 100 ml: 12.1 gr Tris Base, qsp 100 ml H2O MQ, pH 6.8.

Sample Buffer (4×)

For 8 ml: 3.2 ml SDS 10%, 1.6 ml Glicerol, 2 ml Tris-HCl 1 M pH 6.8, 0.8 ml B-Mercaptoethanol, 0.4 ml Bromophenol Blue 0.1% or Red. (Use 1× for experiment)

Running Buffer (10×)

For 1 L: 30.3 g Tris base, 144 gr Glycine, 10 gr SDS, qsp 1 L H2O MQ. (Use 1× for experiment)

The steps for electrophoresis are the following:

a) Prepare the lower and the upper acrilamide gels. The % for APP gel is 10% lower gel and 5% stacking gel.
b) Prepare 24 μl of sample at a concentration of 25 μg (determined by the Bradford Assay) (6 μl SB 4× containing β-mercaptoethanol+protein+lisis) and boil them at 100° C. for 5 minutes to denaturalize them.
c) Put the protein marker and the samples in the wells of the gel (20-30 μL).
d) Proceed to Migration: 35 mA (nearly 1 hour).

Protocol for Western Blot

Before starting the protocol the reagents are prepared as follows:

Transfer Buffer (1×)

For 1 L: 3.03 g Tris base, 14.4 gr Glycine, 200 ml Methanol, qsp 1 L H2O MQ.

TBS Buffer (4×)

For 1 L: 24.25 gr Tris base, 60 gr NaCl, qsp 1 L H2O MQ, pH 7.5.

TBS-Tween Buffer

For 1 L: 250 ml TBS 4×, 0.5 ml Tween 20, qsp 1 L H2O MQ.

There are 2 steps to follow, the electrotransfer and the immunodetection of protein, see the steps below:

1) Electrotransfer
   a) Activate the PVDF membrane: 1 minute in MeOH and 2 minutes in MQ H2O.
   b) Put the PVDF membranes, papers and sponges in Transfer buffer during 10 minutes.
   c) Prepare the sandwich and proceed with the transfer of the proteins from the gel to the PDVF membrane: 0.2 A during 2 hours.

2) Immunodetection of Proteins
   a) Block the inespecific sites of the membrane with milk 5% (dissolve it in TBS-T).
   b) Incubation with the primary antibody (dissolved in TBST/milk 5%): Anti-Amyloid Precursor Protein (ab2072, rabbit) at a dilution 1:500 (20 µl in 10 ml), over-night at 4° C.
   c) Wash the membrane with TBS-T (5 min×2).
   d) Incubation with the secondary antibody dissolved in TBS-T: Anti-rabbit-HRP (goat) dilution 1:5000 (20 µl in 10 ml) for 45 minutes at room temperature.
   e) Wash the membrane with TBS-T (5 min×2+10 min×1).
   f) Take a picture with Chemibox option (white light) to see the position of marker bands.
   g) Add ECL reagent (HRP) for antibody detection (iml of each component) and take several pictures with Chemibox option (no light).

Detailed Methodology: Detection of Aβ42 in Cell Culture Media

After 1 hour of treatment, the culture media was collected and diluted to 1:100, using culture media as diluent. Four repeats of each diluted sample were then placed in the plate provided by the ELISA detection kit, from AnaSpec (Fremont, CA, USA). The detection was then carried out following the manufacturer's protocol. Briefly, the sample was incubated for 4 h in presence of 50 µl of detection antibody. The plate was then washed seven times with the washing solution, the samples were then incubated with the 3,3',5,5'-Tetramethylbenzidine (TMB) provided with the kit for 15 min. after the sample revelation the reaction was stopped with the stop solution and the optical density was read at 450 nm.

Figure 22:
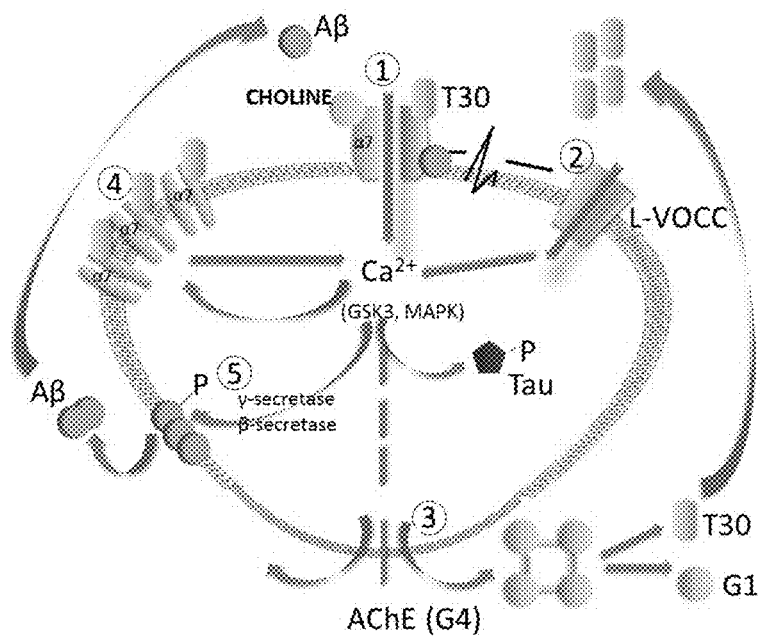
FIG. 22 shows the cascade of events resulting from the effect of T30 in a cell.

FIG. 22 is a diagram showing the cascade of events resulting from the effect of T30 in a cell: (1) T30 binds to the allosteric site of the receptor to enhance the opening of the channel for $Ca^{2+}$ influx into the cell (Greenfield et al. 2004). (2) Calcium entry induces depolarization and opening of the voltage-dependent (L-VOCC) channel allowing still more $Ca^{2+}$ into the cell (Dickinson et al., 2007). (3) This raised intracellular calcium induces an increase in AChE G4 release that includes T30 (Greenfield, 2013). (4) Calcium also induces upregulation of the α7 nicotinic receptor that will allow more $Ca^{2+}$ get in the cell by providing still more targets for T30 (Bond et al., 2009). (5) Calcium activates enzymes (ie GSK-3) that will (a) increase Tau, (b) activate γ-secretase/β-secretase that will trigger cleavage of extracellular toxic Amyloid that (c) together with T30 will promote a still further toxic amount of $Ca^{2+}$ into the cell. (Hartigan & Johnson (1999), Cai et al. (2012), Garcia-Rates et al (2013)).

Accordingly, using immunodetection, the inventors have determined (i) APP levels and (ii) release of amyloid following administration of T30 (5 uM) and NBP14 (0.5 µM).

Figure 23:
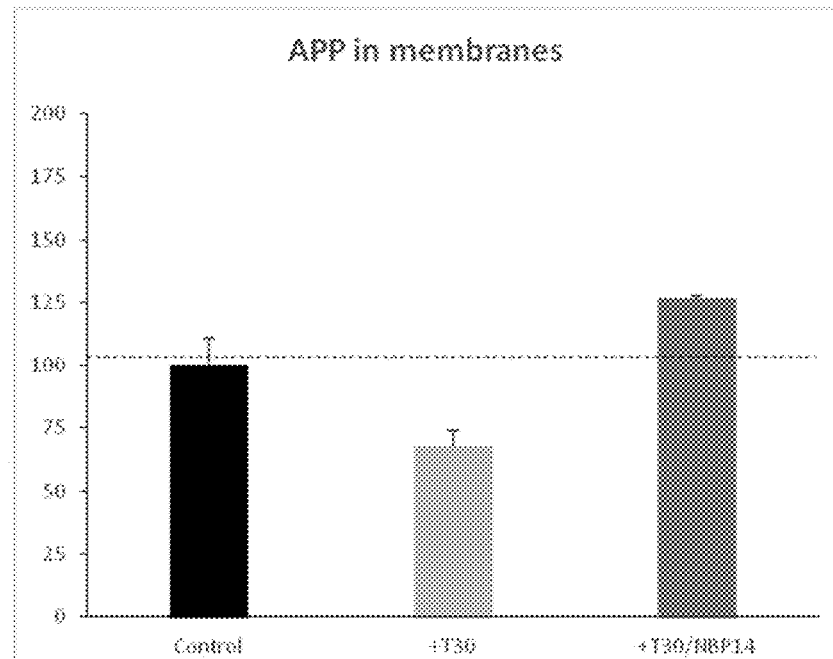
FIG. 23 shows full-length APP is reduced by NBP-14. Data represent expression of APP in solubilized PC12 cells after 3 different 1 hour treatments. Data are represented as mean±SEM, n=2.

Results (i) As shown in FIG. 23, T30 reduces levels of full length APP in PC12 cell membranes, an effect reversed by NBP14. The values are: Control (100%±10.98); T30 5 µM (67.82%±6.23%) and T30+NBP-14 0.5 µM (126%±1.12%).

Figure 24:
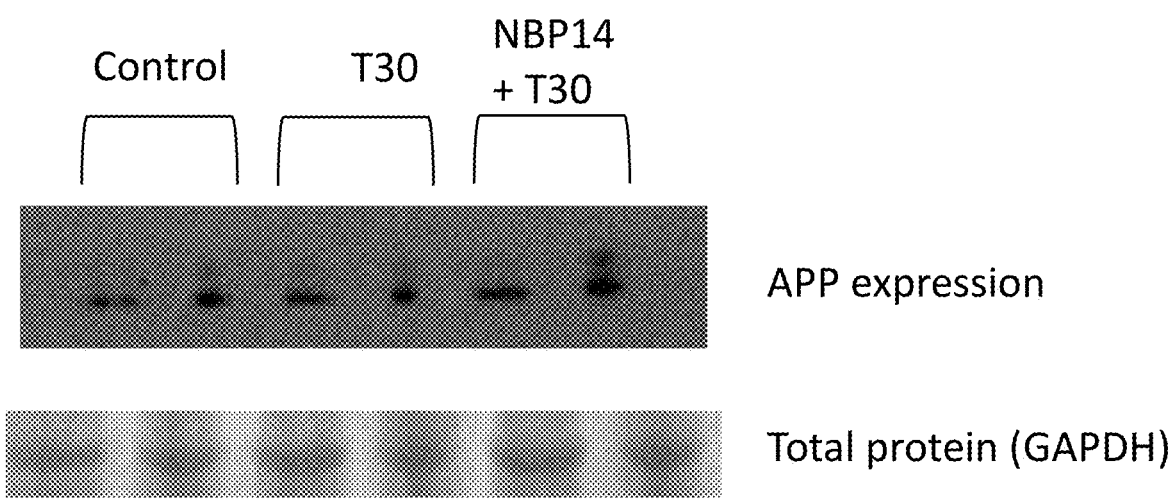
FIG. 24 shows immunodetection by western blot represented in the graph. The 3 different treatments show different levels of expression of APP (values represented in FIG. 24. For each condition protein is corrected by levels of GAPDH.

FIG. 24 shows immunodetection by western blot represented in the graph. The 3 different treatments show different levels of expression of APP (values represented in FIG. 24). For each condition protein is corrected by levels of GAPDH.

The production of APP is reduced by T30 peptide, an effect which is reversed by NBP-14. This suggests that APP could be cleaved, releasing Amyloid-β 1-42 peptide (Aβ42).

Figure 25:
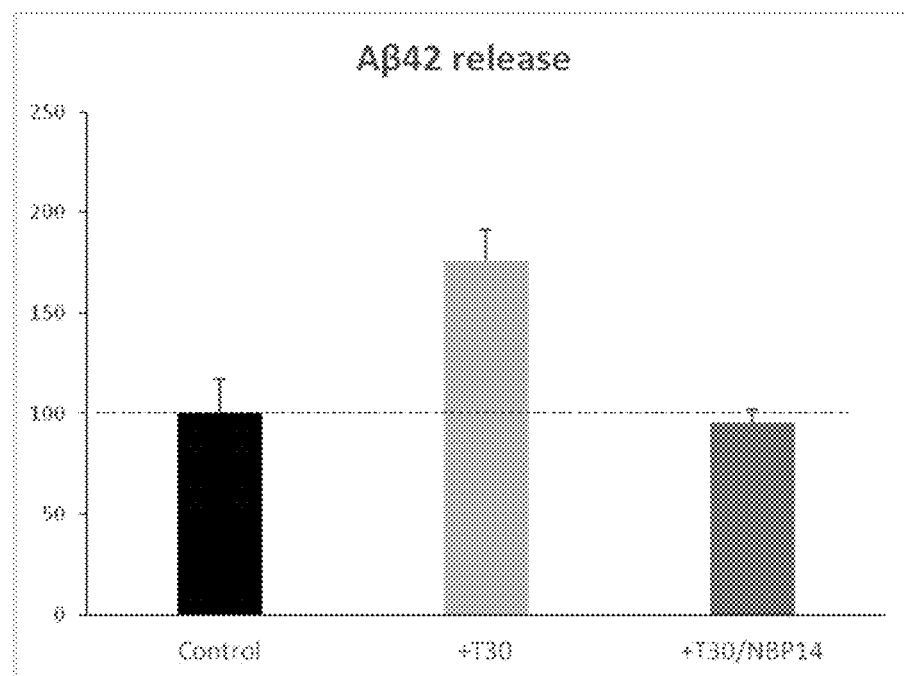
FIG. 25 shows that T30 induces release of Aβ42, an effect reversed by NBP14. Graph showing the release of Aβ42 in control conditions, in presence of T30 and in presence of T30 and NBP-14. The results are represented as mean±SEM (n=4).

(ii) In order to determine the release of Aβ42 we used an ELISA kit, commercially available, measuring Aβ42 present in solution. This test showed that T30 increases the release of Aβ42 up to approximately 175% compared to control and NBP-14 brings the release of Aβ42 to a value close to control (see FIG. 25).

The invention claimed is:

1. A method of treating or ameliorating Alzheimer's Disease in a subject, the method comprising administering to a subject in need of such treatment a therapeutically effective amount of the cyclic polypeptide according to Seq ID No: 4.

* * * * *